(12) United States Patent
Wilson

(10) Patent No.: US 11,366,104 B2
(45) Date of Patent: *Jun. 21, 2022

(54) METHODS OF IDENTIFYING AND MONITORING MITOCHONDRIAL DYSFUNCTION USING MONOCYTE SCREENING

(71) Applicant: Stealth BioTherapeutics Inc., Needham, MA (US)

(72) Inventor: D. Travis Wilson, Newton, MA (US)

(73) Assignee: STEALTH BIOTHERAPEUTICS INC., Needham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/845,687

(22) Filed: Apr. 10, 2020

(65) Prior Publication Data

US 2021/0025873 A1    Jan. 28, 2021

Related U.S. Application Data

(63) Continuation of application No. 15/318,876, filed as application No. PCT/US2015/036130 on Jun. 17, 2015, now Pat. No. 10,627,392.

(60) Provisional application No. 62/013,317, filed on Jun. 17, 2014.

(51) Int. Cl.
    *G01N 33/50*    (2006.01)

(52) U.S. Cl.
    CPC . *G01N 33/5094* (2013.01); *G01N 2800/2835* (2013.01); *G01N 2800/2871* (2013.01); *G01N 2800/325* (2013.01); *G01N 2800/52* (2013.01)

(58) Field of Classification Search
    CPC .................... G01N 33/5094; G01N 2800/2835
    See application file for complete search history.

(56) References Cited

U.S. PATENT DOCUMENTS

| 4,522,811 | A | 6/1985 | Eppstein et al. |
| 4,708,934 | A | 11/1987 | Gilligan et al. |
| 5,674,534 | A | 10/1997 | Zale et al. |
| 5,716,644 | A | 2/1998 | Zale et al. |
| 6,468,798 | B1 | 10/2002 | Debs et al. |
| 10,627,392 | B2 * | 4/2020 | Wilson ............... G01N 33/5094 |
| 2011/0064747 | A1 | 3/2011 | Sarangarajan et al. |
| 2013/0303436 | A1 | 11/2013 | Wilson |
| 2014/0024019 | A1 | 1/2014 | Van Dongen et al. |

FOREIGN PATENT DOCUMENTS

| EP | 0 308 067 A2 | 3/1989 |
| EP | 0 382 403 B1 | 8/1990 |
| WO | WO-96/40073 A2 | 12/1996 |
| WO | WO-99/15154 A1 | 4/1999 |
| WO | WO-2013/055865 | 4/2013 |

OTHER PUBLICATIONS

Xu et al., 2005, Characterization of lymphoblast mitochondria from patients with Barth syndrome, Laboratory Investigation, 85: 823-830.*

Amselem, et al., "A Large-Scale Method for the Preparation of Sterile and Nonpyrogenic Liposomal Formulations of Defined Size Distributions for Clinical Use." Liposome Technology, 1993, vol. I, 2nd ed., CRC Press, pp. 502-525.

Barbiroli et al., "Lipoic (thioctic) acid increases brain energy availability and skeletal muscle performance as shown by in vivo 31P-MRS in a patient with mitochondrial cytopathy." J. Neurol., (1995), vol. 242, Issue 7, pp. 472-477.

Birk et al., 2013, The Mitochondrial-Targeted Compound SS-31 Re-Energizes Ischemic Mitochondria by Interacting with Cardiolipin, X J Am Soc Nephrol, 24: 1250-1261.

Chacko et al., 2013, Methods for defining distinct bioenergetics profiles in platelets, lymphocytes, monocytes, and neutrophils, and the oxidative burst from human blood, Laboratory Investigation, 93: 690-700.

Cho, Sungnee et al., "201CA Novel Cell-permeable Antioxidant Peptide, SS31, Attenuates Ischemic Brain Injury by Down-regulating CD36,201D", J. Biol. Chem., Feb. 2007, vol. 282, No. 7, pp. 4634-4642.

Chonn et al., "Recent Advances in Liposomal Drug-Delivery Systems," Curr. Opin. Biotechnol., Dec. 1995, vol. 6, Issue 6, pp. 698-708.

Dai, Dao-Fu et al., "Mitochondrial targeted antioxidant peptide ameliorates hypertensive cardiomyopathy," J. Am. Coll. Cardiol., Jun. 28, 2011, vol. 58, No. 1, pp. 73-82.

Erhola et al. "Biomarker evidence of DNA oxidation in lung cancer patients: association of urinary 8-hydroxy-2'-deoxyguanosine excretion with radiotherapy, chemotherapy, and response to treatment." FEBS Lett, (1997), vol. 409, Issue 2, pp. 287-291.

Fabrizi et al. "Autosomal dominant limb girdle myopathy with ragged-red fibers and cardiomyopathy. A pedigree study by in vivo 31P-MR spectroscopy indicating a multisystem mitochondrial defect." J. Neurol. Sci., (1996), vol. 137, Issue 1, pp. 20-27.

Fabrucius et al., 2010, Measure of expression of mitochondrial related genes in human mononuclear blood cells, adipose white tissue and smooth muscle cells, Clinica Chimica Acta, 411: 749-753.

Gnaiger. "Mitochondrial Pathways and Respiratory Control: An Introduction to OXPHOS Analysis." 3rd ed., Oroboros Instruments (2012), pp. 1-64.

Gregoriadis, "Engineering Liposomes for Drug Delivery: Progress and Problems," Trends in Biotechnology, Dec. 1995, vol. 13, No. 12, pp. 527-537.

Honda et al., "Correlation of urinary 8-hydroxy-2%-deoxyguanosine (8-OHdG), a biomarker of oxidative DNA damage, and clinical features of hematological disorders: a pilot study." Leukemia Res., (2000), vol. 24, Issue 6, pp. 461-468.

International Search Report and Written Opinion in International Patent Application No. PCT/US2015/036130 dated Sep. 21, 2015.

Kaufmann et al. "Cerebral lactic acidosis correlates with neurological impairment in MELAS." Neurology, (2004), vol. 62, Issue 8, pp. 1297-1302.

(Continued)

*Primary Examiner* — Amber D Steele

(74) *Attorney, Agent, or Firm* — Foley & Lardner LLP

(57) ABSTRACT

The present technology provides methods for detecting and diagnosing diseases and conditions characterized by mitochondrial dysfunction using monocytes as an indicator of the dysfunction.

20 Claims, 8 Drawing Sheets

(56) References Cited

OTHER PUBLICATIONS

Kim et al. "Urinary 8-Hydroxy-2'-Deoxyguanosine as a Biomarker of Oxidative DNA Damage in Workers Exposed to Fine Particulates." Environ. Health Perspect., (2004), vol. 112, Issue 6, pp. 666-671.
Kozarich, et al., "Next generation therapeutics: Looking to the horizon: Editorial overview," Curr. Opin. Chem. Biol., 1998, vol. 2, Issue 4, pp. 439-440.
Kunz et al., 1997, Flow Cytometric Detection of Mitchondrial Dysfunction in Subpopulations of Human Mononuclear Cells, Analytical Biochemistry, 246: 218-224.
Lichtenberg, et al., "Liposomes: Preparation, Characterization, and Preservation," Methods Biochem. Anal., 1998, vol. 33, pp. 337-462.
Lunnon et al., 2012, Mitochondrial Dysfunction and Immune Activation are Detectable in Early Alzheimer's Disease Blood, Journal of Alzheimer's Disease, 30: 685-710.
Manczak, Mana et al., "Mitochondria-Targeted Antioxidants protect Against Amyioid-β toxicity in Alzheimer's Disease Neurons," J. Alzheimer's Dis., (2010), 20, pp. S609-S631.
Matthews et al., "In vivo magnetic resonance spectroscopy of brain and muscle in a type of mitochondrial encephalomyopathy (MERRF)." Ann. Neurol., (1991), vol. 29, Issue 4, pp. 435-438.
Min, Kisuk et al., "Mitochondrial-targeted antioxidants protect skeletal muscle against immobilization-induced muscle atrophy," J. Appl. Physiol., (2011), 111(5), pp. 1459-1466.
Mizuguchi, et al., "Intratumor administration of fusogenic liposomes containing fragment A of diphtheria toxin suppresses tumor growth." Cancer Lett., Feb. 26, 1996, vol. 100, Issue 1, pp. 63-69.
Munnich et al., "Clinical Aspects of Mitochondrial Disorders." J. Inherit. Metab. Dis., (1992), vol. 15, Issue 4, pp. 448-455.
Notice of Allowance in U.S. Appl. No. 15/318,876 dated Dec. 17, 2019.
Petri, et al., "Cell-permeable peptide antioxidants as a novel therapeutic approach in a mouse model of amyotrophic lateral sclerosis," Journal of Neurochemistry, 2006, pp. 1141-1148, vol. 98.
Pilger et al., "Longitudinal study of urinary 8-hydroxy-2'-deoxyguanosine excretion in healthy adults." Free Radic. Res., (2001), vol. 35, Issue 3, pp. 273-280.
Powers et al., 2011, Mitochondrial-targeted antioxidants protect against mechanical ventilation-induced diaphragm weakness, Crit V Care Med, 39(7): 1749-1759.
Reddy, "Controlled-Release, Pegylation, Liposomal Formulations: New Mechanisms in the Delivery of Injectable Drugs," Ann Pharmacother., Jul./Aug. 2000, vol. 34, pp. 915-923.
Rolfe. "In vivo near-infrared spectroscopy," Ann. Rev. Biomed. Eng., (2000), vol. 2, pp. 715-754.
Siegel et al., 2013, Mitochondrial targeted peptide rapidly improves mitochondrial energetics and skeletal muscle performance in aged mice, Aging Cell, 12(5): 763-771.
Strangman. "Non-invasive neuroimaging using near-infrared light." Biol. Psychiatry, (2002), vol. 52, pp. 679-693.
Szeto et al., "Mitochondria-Targeted Peptide Accelerates ATP Recovery and Reduces Ischemic Kidney Injury," Journal of the American Society of Nephrol, vol. 22, No. 6, Jun. 1, 2011, pp. 1041-1052.
Szeto et al., "Novel Therapies Targeting Inner Mitochondrial Membrane—From Discovery to Clinical Development" Pharm Res, vol. 28, 2001, pp. 2669-2679.
Szeto, 2008, Mitochondria-Targeted Cytoprotective Peptides for Ischemia-Reperfusion Injury, Antioxidants, 10(3): 601-619.
Szeto, et al., "Novel Therapies Targeting Inner Mitochondrial Membrane—from Discovery to Clinical Development", Pharm. Res., (2011), vol. 28, pp. 2669-2679.
Szeto, Hazel H. "Mitochondria-targeted peptide antioxidants: Novel Neuroprotective Agents," The AAPS Journal, (2006), 8(3), Article 62, pp. E521-E531.
Ueda et al. "Evaluation of Changes in Hepatic Energy Metabolism During Exercise by Ketone Body Ratio in Humans." J. Cardiol., (1997), vol. 29, Issue 2, pp. 95-102.
Weiner, Alan L., "Liposomes for Protein Delivery: Selecting Manufacture and Development Processes," Immunomethods, Jun. 1994, vol. 4, No. 3, pp. 201-209.
Wu et al. "A highly potent peptide analgesic that protects against ischemia-reperfusion-induced myocardial stunning", Am. J. Physiol. Heart. Circ. Physiol., Aug. 2002, vol. 283, No. 2, pp. H783-H791.
Zang et al., 2010, Burn serum causes a CD 14-dependent mitochondrial damage in primary cardiomyocytes, Am J Physiol Heart u Circ Physiol, 298(6): H1951-H1958.
Zhao et al., "Cell-permeable Peptide Antioxidants Targeted to Inner Mitochrondrial Membramne inhibit Mitochondrial Swelling, Oxidative Cell Death, and Reperfusion Injury," J. Biol. Chem. 279: 34682-34690 (2004).
Zhao, et al., "Transcellular Transport of a Highly Polar 3+ Net Charge Opioid Tetrapeptide," Journal of Pharmacology and Experimental Therapeutics, 2003, vol. 304, No. 1, pp. 425-432.
Zhao, Kesheng et al., "Mitochondria-targeted peptide prevents mitochondrial depolarization and apoptosis induced by tert-butyl hydroperoxide in neuronal cell lines," Biochem. Pharmacol., (2005), 70, pp. 1796-1806.
Canadian First Office Action on CA Patent Application No. 2952615 dated Jul. 29, 2021 (4 pages).
Chariot et al. "Optimal Handling of Blood Samples for Routine Measurement of Lactate and Pyruvate." Arch. Pathol. Lab. Med., (1194), vol. 118, Issue 7, Jul. 1994, pp. 695-697.
Szeto, H. "Development of Mitochondria-targeted Aromatic-cationic Peptides for Neurodegenerative Diseases," Ann. N.Y. Acad. Sci., 2008, vol. 1147, pp. 112-121.
Szeto, Hazel H., "Cell-permeable, Mitochondrial-targeted, Peptide Antioxidants," The AAPS Journal, 2006, vol. 8, No. 2, Article 32, pp. E277-E283.

* cited by examiner

FIG. 1A

Treatment with D-Arg-2'6'Dmt-Lys-Phe-NH$_2$

OCR = oxygen consumption rate

MCs = isolated monocytes

AWAKE Conscious

Dog No. 13-016        OCR, pmols/ug Protein

| Parameters | DAY 0--BL | DAY 0--4 hr | DAY 1--24 hrs | DAY 2--48 hrs | DAY 3--72 hrs | DAY 4--96 hrs | DAY 7--168 hrs |
|---|---|---|---|---|---|---|---|
| Basal Respiration | 4.8 | 6.8 | 7.4 | 15.6 | 11.2 | 8.3 | 6.9 |
| Proton Leak | 0.4 | 0.8 | 1.4 | 6.4 | 0.9 | 0.7 | 1.0 |
| ATP Production linked Respiration | 4.4 | 6.0 | 6.0 | 9.3 | 10.3 | 7.6 | 5.9 |
| Maximal Respiration | 13.4 | 17.2 | 25.7 | 38.9 | 23.3 | 18.7 | 13.9 |
| Respiratory Capacity | 9.0 | 11.2 | 19.7 | 29.6 | 13.1 | 11.1 | 8.0 |
| Non Mitochondrial | 3.0 | 3.4 | 3.1 | 4.1 | 3.0 | 2.7 | 1.8 |
| Viability of Isolated MCs (%) | 67 | 67 | 68 | 77 | 65 | 63 | 64 |

AWAKE Conscious

Dog No. 13-014        OCR, pmols/min/ug Protein

| Parameters | DAY 0--BL | DAY 0--4 hr | DAY 1--24 hrs | DAY 2--48 hrs | DAY 3--72 hrs | DAY 4--96 hrs | DAY 7--168 hrs |
|---|---|---|---|---|---|---|---|
| Basal Respiration | 5.2 | 6.8 | 8.9 | 15.7 | 11.3 | 7.9 | 7.8 |
| Proton Leak | 0.4 | 0.7 | 1.6 | 1.8 | 0.7 | 0.4 | 1.5 |
| ATP Production linked Respiration | 4.7 | 6.2 | 7.3 | 13.9 | 10.6 | 7.5 | 6.2 |
| Maximal Respiration | 14.9 | 19.9 | 25.4 | 45.4 | 34.4 | 27.8 | 18.7 |
| Respiratory Capacity | 10.1 | 13.7 | 18.1 | 31.5 | 23.8 | 20.3 | 12.4 |
| Non Mitochondrial | 2.2 | 2.3 | 3.1 | 5.2 | 5.2 | 3.9 | 2.4 |
| Viability of Isolated MCs (%) | 82.0 | 82.0 | 84.0 | 83.0 | 80.0 | 82.0 | 81.0 |

FIG. 1A (cont.)

| AWAKE Conscious | | | | | | | |
|---|---|---|---|---|---|---|---|
| Dog No. 14-028 | OCR, pmols/min/ug Protein | | | | | | |
| Parameters | DAY 0--BL | DAY 0--4 hr | DAY 1--24 hrs | DAY 2--48 hrs | DAY 3--72 hrs | DAY 4--96 hrs | DAY 7--168 hrs |
| Basal Respiration | 5.60 | 6.30 | 8.24 | 12.25 | 10.83 | 11.86 | 6.07 |
| Proton Leak | 1.26 | 1.02 | 0.35 | 3.28 | 2.55 | 3.73 | 2.25 |
| ATP Production linked Respiration | 4.35 | 5.27 | 7.89 | 8.97 | 8.28 | 8.12 | 3.81 |
| Maximal Respiration | 13.52 | 14.69 | 17.82 | 53.15 | 33.01 | 26.25 | 7.86 |
| Respiratory Capacity | 9.17 | 9.41 | 9.93 | 44.18 | 24.72 | 18.13 | 4.05 |
| Non Mitochondrial | 3.63 | 3.32 | 4.69 | 7.16 | 6.96 | 5.62 | 3.49 |
| Viability of Isolated MCs (%) | 79 | 76 | 70 | 75 | 72 | 70 | 74 |

FIG. 1B

Treatment with Saline

OCR = oxygen consumption rate

MCs = isolated monocytes

AWAKE Conscious

| Dog No. 14-040 | OCR, pmols/ug Protein | | | | | | |
|---|---|---|---|---|---|---|---|
| Parameters | DAY 0- -BL | DAY 0- -4 hr | DAY 1- -24 hrs | DAY 2- -48 hrs | DAY 3- -72 hrs | DAY 4- -96 hrs | DAY 7-- 168 hrs |
| Basal Respiration | 4.75 | 4.05 | 5.54 | 4.97 | 13.10 | 5.06 | 6.30 |
| Proton Leak | 0.78 | 0.45 | 0.70 | 0.32 | 14.14 | 0.36 | 5.83 |
| ATP Production linked Respiration | 3.98 | 3.59 | 4.84 | 4.65 | -1.04 | 4.70 | 0.47 |
| Maximal Respiration | 15.87 | 13.03 | 22.19 | 18.51 | 12.21 | 14.32 | 19.78 |
| Respiratory Capacity | 11.89 | 9.44 | 17.35 | 13.86 | 13.25 | 9.62 | 19.31 |
| Non Mitochondrial | 2.49 | 1.60 | 1.91 | 3.52 | 8.77 | 2.00 | 3.68 |
| Viability of Isolated MCs (%) | 75 | 68 | 77 | 78 | 60 | 80 | 60 |

AWAKE Conscious

| Dog No. 14-054 | OCR, pmols/ug Protein | | | | | | |
|---|---|---|---|---|---|---|---|
| Parameters | DAY 0- -BL | DAY 0- -4 hr | DAY 1- -24 hrs | DAY 2- -48 hrs | DAY 3- -72 hrs | DAY 4- -96 hrs | DAY 7-- 168 hrs |
| Basal Respiration | 6.94 | 5.71 | 6.65 | 6.54 | 6.61 | 6.67 | 6.57 |
| Proton Leak | 2.49 | 1.30 | 3.77 | 1.64 | 2.63 | 0.89 | 6.06 |
| ATP Production linked Respiration | 4.46 | 4.41 | 2.88 | 4.90 | 3.98 | 5.78 | 0.51 |
| Maximal Respiration | 7.59 | 13.05 | 16.10 | 17.78 | 13.84 | 15.41 | 14.47 |
| Respiratory Capacity | 3.14 | 8.63 | 13.22 | 12.88 | 9.86 | 9.63 | 13.96 |
| Non Mitochondrial | 1.90 | 1.68 | 3.18 | 3.16 | 2.60 | 3.13 | 2.83 |
| Viability of Isolated MCs (%) | 65 | 67 | 68 | 61 | 60 | 56 | 50 |

FIG. 1B (cont.)

| AWAKE Conscious | | | | | | | |
|---|---|---|---|---|---|---|---|
| Dog No. 14-056 | OCR, pmols/min/ug Protein | | | | | | |
| Parameters | DAY 0-BL | DAY 0-4 hr | DAY 1-24 hrs | DAY 2-48 hrs | DAY 3-72 hrs | DAY 4-96 hrs | DAY 7-168 hrs |
| Basal Respiration | 5.34 | 5.27 | 4.78 | 4.76 | 4.76 | 6.19 | 5.92 |
| Proton Leak | 2.49 | 3.47 | 3.01 | 2.24 | 1.45 | 2.21 | 1.67 |
| ATP Production linked Respiration | 2.86 | 1.79 | 1.77 | 2.52 | 3.31 | 3.98 | 4.25 |
| Maximal Respiration | 14.11 | 10.67 | 16.57 | 17.40 | 19.33 | 18.20 | 7.90 |
| Respiratory Capacity | 11.25 | 8.88 | 14.81 | 14.87 | 16.02 | 14.22 | 3.65 |
| Non Mitochondrial | 2.40 | 2.04 | 2.93 | 3.01 | 2.74 | 2.30 | 2.56 |
| Viability of Isolated MCs (%) | 66 | 67 | 68 | 62 | 63 | 58 | 55 |

FIG. 1C

Treatment with Saline

| | | | | | | | | |
|---|---|---|---|---|---|---|---|---|
| D14-040 | ATP Production linked Respiration | 3.98 | 3.59 | 4.84 | 4.65 | -1.04 | 4.70 | 0.47 |
| D14-054 | ATP Production linked Respiration | 4.46 | 4.41 | 2.88 | 4.90 | 3.98 | 5.78 | 0.51 |
| D14-056 | ATP Production linked Respiration | 2.86 | 1.79 | 1.77 | 2.52 | 3.31 | 3.98 | 4.25 |
| | Mean | 3.76 | 3.27 | 3.16 | 4.03 | 2.08 | 4.82 | 1.74 |
| | STD | 0.82 | 1.34 | 1.56 | 1.31 | 2.73 | 0.91 | 2.17 |
| | SEM | 0.47 | 0.77 | 0.90 | 0.75 | 1.57 | 0.52 | 1.25 |

Treatment with D-Arg-2'6'Dmt-Lys-Phe-NH$_2$

| | | | | | | | | |
|---|---|---|---|---|---|---|---|---|
| D13-016 | ATP Production linked Respiration | 4.42 | 6.04 | 6.01 | 9.26 | 10.29 | 7.60 | 5.94 |
| D13-014 | ATP Production linked Respiration | 4.74 | 6.17 | 7.29 | 13.91 | 10.58 | 7.53 | 6.23 |
| D14-028 | ATP Production linked Respiration | 4.35 | 5.27 | 7.89 | 8.97 | 8.28 | 8.12 | 3.81 |
| | Mean | 4.50 | 5.83 | 7.06 | 10.71 | 9.72 | 7.75 | 5.33 |
| | STD | 0.21 | 0.48 | 0.96 | 2.77 | 1.25 | 0.32 | 1.32 |
| | SEM | 0.12 | 0.28 | 0.56 | 1.60 | 0.72 | 0.19 | 0.76 |
| P-value vs. Saline | | NS | 0.035 | 0.020 | 0.019 | 0.011 | 0.006 | NS |

FIG. 1C (cont.)

Treatment with Saline

| | | | | | | | | | |
|---|---|---|---|---|---|---|---|---|---|
| D14-040 | Maximal Respiration | | 15.9 | 13.0 | 22.2 | 18.5 | 12.2 | 14.3 | 19.8 |
| D14-054 | Maximal Respiration | | 7.6 | 13.0 | 16.1 | 17.8 | 13.8 | 15.4 | 14.5 |
| D14-056 | Maximal Respiration | | 14.1 | 10.7 | 16.6 | 17.4 | 19.3 | 18.2 | 7.9 |
| | | Mean | 12.5 | 12.2 | 18.3 | 17.9 | 15.1 | 16.0 | 14.1 |
| | | STD | 4.4 | 1.4 | 3.4 | 0.6 | 3.7 | 2.0 | 6.0 |
| | | SEM | 2.5 | 0.8 | 2.0 | 0.3 | 2.2 | 1.2 | 3.4 |

Treatment with D-Arg-2'6'Dmt-Lys-Phe-NH$_2$

| | | | | | | | | | |
|---|---|---|---|---|---|---|---|---|---|
| D13-016 | Maximal Respiration | | 13.4 | 17.2 | 25.7 | 38.9 | 23.3 | 18.7 | 13.9 |
| D13-014 | Maximal Respiration | | 14.9 | 19.9 | 25.4 | 45.4 | 34.4 | 27.8 | 18.7 |
| D14-028 | Maximal Respiration | | 13.5 | 14.7 | 17.8 | 53.2 | 33.0 | 26.2 | 7.9 |
| | | Mean | 13.9 | 17.2 | 23.0 | 45.8 | 30.3 | 24.3 | 13.5 |
| | | STD | 0.8 | 2.6 | 4.5 | 7.1 | 6.0 | 4.9 | 5.4 |
| | | SEM | 0.5 | 1.5 | 2.6 | 4.1 | 3.5 | 2.8 | 3.1 |
| | P-value vs. Saline | | NS | 0.042 | NS | 0.002 | 0.021 | 0.05 | NS |

FIG. 1C (cont.)

Treatment with Saline

| D14-040 | Respiratory Capacity | | 11.89 | 9.44 | 17.35 | 13.86 | 13.25 | 9.62 | 19.31 |
|---|---|---|---|---|---|---|---|---|---|
| D14-054 | Respiratory Capacity | | 3.14 | 8.63 | 13.22 | 12.88 | 9.86 | 9.63 | 13.96 |
| D14-056 | Respiratory Capacity | | 11.25 | 8.88 | 14.81 | 14.87 | 16.02 | 14.22 | 3.65 |
| | | Mean | 8.8 | 9.0 | 15.1 | 13.9 | 13.0 | 11.2 | 12.3 |
| | | STD | 4.9 | 0.4 | 2.1 | 1.0 | 3.1 | 2.7 | 8.0 |
| | | SEM | 2.8 | 0.2 | 1.2 | 0.6 | 1.8 | 1.5 | 4.6 |

Treatment with D-Arg-2'6'Dmt-Lys-Phe-NH$_2$

| D13-016 | Respiratory Capacity | | 9.0 | 11.2 | 19.7 | 29.6 | 13.1 | 11.1 | 8.0 |
|---|---|---|---|---|---|---|---|---|---|
| D13-014 | Respiratory Capacity | | 10.1 | 13.7 | 18.1 | 31.5 | 23.8 | 20.3 | 12.4 |
| D14-028 | Respiratory Capacity | | 9.17 | 9.41 | 9.93 | 44.18 | 24.72 | 18.13 | 4.05 |
| | | Mean | 9.4 | 11.4 | 15.9 | 35.1 | 20.5 | 16.5 | 8.1 |
| | | STD | 0.6 | 2.2 | 5.2 | 7.9 | 6.5 | 4.8 | 4.2 |
| | | SEM | 0.4 | 1.2 | 3.0 | 4.6 | 3.7 | 2.8 | 2.4 |
| | P-value vs. Saline | | NS | NS | NS | 0.01 | NS | NS | NS |

FIG. 2

| Site of Dysfunction | Biochemical Event | Measurable Energy Biomarker | Physical Effect |
|---|---|---|---|
| Respiratory Chain | ↑ NADH | Δ lactate, Δ lactate:pyruvate ratio; and Δ acetoacetate:β-hydroxy butyrate ratio | Metabolic dyscrasia & fatigue |
| Respiratory Chain | ↓ $H^+$ gradient | Δ ATP | Organ dependent dysfunction |
| Respiratory Chain | ↓ Electron flux | Δ $VO_2$, RQ, BMR, AT, AT, pH | Metabolic dyscrasia & fatigue |
| Mitochondria & cytosol | ↓ ATP, ↓ $VO_2$ | Δ Work, ΔHR (CO) | Exercise intolerance |
| Mitochondria & cytosol | ↓ ATP | Δ PCr | Exercise intolerance |
| Respiratory Chain | ↓ Cyt $C_{Ox/Red}$ | Δλ ~700–900 nM (Near Infrared Spectroscopy) | Exercise intolerance |
| Intermediary metabolism | ↓ Catabolism | Δ $C^{14}$-Labeled substrates | Metabolic dyscrasia & fatigue |
| Respiratory Chain | ↓ Electron flux | Δ Mixed Venous $VO_2$ | Metabolic dyscrasia & fatigue |
| Mitochondria & cytosol | ↑ Oxidative stress | Δ Tocopherol & Tocotrienols, CoQ10, docosahexanoic acid | Uncertain |
| Mitochondria & cytosol | ↑ Oxidative stress | Δ $Glutathione_{red}$ | Uncertain |
| Mitochondria & cytosol | Nucleic acid oxidation | Δ8-hydroxy 2-deoxy guanosine | Uncertain |
| Mitochondria & cytosol | Lipid oxidation | ΔIsoprostane(s), eicasanoids | Uncertain |
| Cell membranes | Lipid oxidation | ΔEthane (breath) | Uncertain |
| Cell membranes | Lipid oxidation | ΔMalondialdehyde | Uncertain |

METHODS OF IDENTIFYING AND MONITORING MITOCHONDRIAL DYSFUNCTION USING MONOCYTE SCREENING

CROSS-REFERENCE TO RELATED APPLICATIONS

This application is a continuation of U.S. application Ser. No. 15/318,876, filed Dec. 14, 2016, now U.S. Pat. No. 10,627,392, issued Apr. 21, 2020, which is a 371c National Phase Entry of PCT/US2015/036130, filed Jun. 17, 2015, which claims the benefit of and priority to U.S. Application No. 62/013,317, filed Jun. 17, 2014, the contents of which are incorporated herein by reference in their entireties.

TECHNICAL FIELD

The present technology relates generally to methods for detecting and diagnosing diseases and conditions characterized by mitochondrial dysfunction using monocytes as an indicator of the dysfunction.

BACKGROUND

The following description is provided to assist the understanding of the reader. None of the information provided or references cited is admitted to be prior art.

Many chronic pathological conditions associated with mitochondrial dysfunction such as metabolic syndrome, diabetes, neurodegenerative diseases, and atherosclerosis are associated with an inflammatory response with the release of proinflammatory mediators, particularly cytokines. Monocytes are phagocytic cells that play an important role in the innate immune system. Once secreted from the bone marrow into the blood, these cells survey the body for sites of inflammation. On encountering inflammatory stress signals the monocytes must rapidly activate and migrate to areas of injury where they can differentiate into the pro-inflammatory "killer" (M1) or anti-inflammatory "repair" (M2) phenotype. Both human classical and intermediate monocytes have inflammatory properties that are reminiscent of M1 phenotype, while non-classical monocytes display properties similar to M2 phenotype.

In the M1 state, the activated monocyte-macrophage cell undergoes a metabolic switch from oxidative phosphorylation to glycolysis. This switch is important because it provides substrates for biosynthetic programs, maintains mitochondrial membrane potential and results in ATP production within the cell. Inhibition of oxidative phosphorylation also increases reactive oxygen species (ROS) production which exerts bactericidal activities. During the resolution of inflammation, the macrophages transform into the alternatively activated M2 phenotype and a more oxidative phosphorylation phenotype. Thus, the metabolic programs of monocyte/macrophage populations are highly plastic and adapt to facilitate the changing function of these cells in the inflammatory process. Currently, it is unclear whether early changes in metabolic phenotype associated with exposure to pro-inflammatory conditions can be detected in the pre-differentiated circulating monocytes.

SUMMARY OF THE PRESENT TECHNOLOGY

There is a need for accurate and sensitive methods that permit the identification and monitoring of a broad range of pathological conditions including but not limited to ischemia, stroke, renal injury, neurodegenerative diseases, atherosclerosis, metabolic syndrome, acute myocardial infarction, heart failure, ischemia reperfusion, ureteral obstruction, diabetic nephropathy, diabetes, Leber's Heredity Optic Neuropathy (LHON), Dominant Optic Atrophy (DOA), Barth's syndrome, POLG disease and Leigh's disease.

In one aspect, the present technology provides a method for identifying a disease or condition characterized by mitochondrial dysfunction in a subject, comprising (a) assaying the level of a population of activated monocytes present in a biological sample obtained from the subject, and (b) comparing the level of the population of activated monocytes observed in step (a) with the level of a corresponding population of activated monocytes observed in a reference sample, wherein the subject is identified as having a disease or condition characterized by mitochondrial dysfunction if the level of the population of activated monocytes present in the biological sample is increased compared to the reference sample.

In some embodiments, the reference sample is a biological sample obtained from a healthy subject.

In some embodiments, the total count of activated monocytes present in the biological sample is increased compared to the reference sample. In some embodiments, the level of classical monocytes ($CD14^{high}$ $CD16^-$) is elevated compared to the reference sample. In some embodiments, the level of intermediate monocytes ($CD14^{high}CD16^+$) is elevated compared to the reference sample. In a further embodiment, the level of non-classical monocytes ($CD14^{low}CD16^{high}$) is decreased compared to the reference sample. In some embodiments, the monocytes are circulating monocytes. In other embodiments, the monocytes are extravasated from the bloodstream to other tissues.

In some embodiments, the disease or condition characterized by mitochondrial dysfunction is ischemia, stroke, renal injury, neurodegenerative disease, atherosclerosis, metabolic syndrome, acute myocardial infarction, heart failure, ischemia reperfusion, ureteral obstruction, diabetic nephropathy, diabetes, Leber's Heredity Optic Neuropathy (LHON), Dominant Optic Atrophy (DOA), Barth's syndrome, POLG disease, or Leigh's disease. In some embodiments, the neurodegenerative disease is Alzheimer's disease, Amyotrophic Lateral Sclerosis (ALS), Huntington's disease, Friedreich's ataxia or Multiple Sclerosis.

In another embodiment, the present technology provides a method for identifying a disease or condition characterized by mitochondrial dysfunction in a subject, comprising (a) assaying the ratio of different monocyte types present in a biological sample obtained from the subject, and (b) comparing the ratio of different monocyte types observed in step (a) with the ratio of corresponding monocyte types observed in a reference sample, wherein the subject is identified as having a disease or condition characterized by mitochondrial dysfunction if the ratio of different monocyte types present in the biological sample is altered compared to the reference sample.

In some embodiments, the reference sample is a biological sample obtained from a healthy subject. In some embodiments, the monocytes are circulating monocytes. In other embodiments, the monocytes are extravasated from the bloodstream to other tissues. In some embodiments, the ratio of activated monocytes to non-classical monocytes is elevated compared to the reference sample. In some embodiments, the ratio of classical monocytes to non-classical monocytes is elevated compared to the reference sample. In some embodiments, the ratio of intermediate monocytes to non-classical monocytes is elevated compared to the reference sample. In certain embodiments, the ratio of classical monocytes to intermediate monocytes is elevated compared to the reference sample.

In some embodiments, the disease or condition characterized by mitochondrial dysfunction is ischemia, stroke, renal injury, neurodegenerative disease, atherosclerosis, metabolic syndrome, acute myocardial infarction, heart failure, ischemia reperfusion, ureteral obstruction, diabetic nephropathy, diabetes, Leber's Heredity Optic Neuropathy (LHON), Dominant Optic Atrophy (DOA), Barth's syndrome, POLG disease, or Leigh's disease. In some embodiments, the neurodegenerative disease is Alzheimer's disease, Amyotrophic Lateral Sclerosis (ALS), Huntington's disease, Friedreich's ataxia or Multiple Sclerosis.

In another embodiment, the present technology provides a method for identifying a disease or condition characterized by mitochondrial dysfunction in a subject, comprising (a) assaying at least one biomarker of mitochondrial physiology of a population of monocytes present in a biological sample obtained from the subject, and (b) comparing the biomarker of mitochondrial physiology of the population of monocytes observed in step (a) with the biomarker of mitochondrial physiology of a corresponding population of monocytes observed in a reference sample, wherein the subject is identified as having a disease or condition characterized by mitochondrial dysfunction if the biomarker of mitochondrial physiology of the population of monocytes present in the biological sample is altered compared to the reference sample.

In some embodiments, the reference sample is a biological sample obtained from a healthy subject. In some embodiments, the monocytes are circulating monocytes. In other embodiments, the monocytes are extravasated from the bloodstream to other tissues.

In some embodiments, the disease or condition characterized by mitochondrial dysfunction is ischemia, stroke, renal injury, neurodegenerative disease, atherosclerosis, metabolic syndrome, acute myocardial infarction, heart failure, ischemia reperfusion, ureteral obstruction, diabetic nephropathy, diabetes, Leber's Heredity Optic Neuropathy (LHON), Dominant Optic Atrophy (DOA), Barth's syndrome, POLG disease, or Leigh's disease. In some embodiments, the neurodegenerative disease is Alzheimer's disease, Amyotrophic Lateral Sclerosis (ALS), Huntington's disease, Friedreich's ataxia or Multiple Sclerosis.

In some embodiments, the disease or condition characterized by mitochondrial dysfunction results in a disruption in oxidative phosphorylation.

In some embodiments, alterations in the biomarkers of mitochondrial physiology of monocytes can be determined by assaying levels of one or more biomarkers of mitochondrial physiology selected from the group consisting of lactic acid (lactate) levels, pyruvic acid (pyruvate) levels, lactate/pyruvate ratios, phosphocreatine levels, NADH (NADH+H$^{30}$) or NADPH (NADPH+H$^{30}$) levels; NAD or NADP levels; ATP levels; reduced coenzyme Q (CoQred) levels; oxidized coenzyme Q (CoQox) levels; total coenzyme Q (CoQtot) levels; oxidized cytochrome C levels; reduced cytochrome C levels; oxidized cytochrome C/reduced cytochrome C ratio; acetoacetate levels; beta-hydroxy butyrate levels; acetoacetate/beta-hydroxy butyrate ratio; 8-hydroxy-2'-deoxyguanosine (8-OHdG) levels; levels of reactive oxygen species; oxygen consumption (VO2), carbon dioxide output (VCO2), and respiratory quotient (VCO2/VO2).

One aspect of the present technology provides a method for evaluating the therapeutic efficacy of an aromatic-cationic peptide on a disease or condition characterized by mitochondrial dysfunction in a subject, comprising (a) assaying the level of a population of activated monocytes present in a biological sample obtained from the subject, and (b) comparing the level of the population of activated monocytes observed in step (a) with the level of a corresponding population of activated monocytes observed in a biological sample obtained from the subject following administration of a dose of an aromatic-cationic peptide, wherein the aromatic-cationic peptide is identified as having a therapeutic effect on the disease or condition characterized by mitochondrial dysfunction if the level of the population of activated monocytes in the biological sample following the administration of the aromatic-cationic peptide is reduced compared to the level of the population of activated monocytes observed in step (a).

In some embodiments, the aromatic-cationic peptide is Phe-D-Arg-Phe-Lys-NH$_2$ or D-Arg-2'6'Dmt-Lys-Phe-NH$_2$ or a pharmaceutically acceptable salt thereof.

In some embodiments, the level of classical monocytes (CD14$^{high}$ CD16$^-$) in the biological sample following the administration of the aromatic-cationic peptide is reduced compared to the level of classical monocytes observed in step (a). In some embodiments, the level of intermediate monocytes (CD14$^{high}$CD16$^+$) in the biological sample following the administration of the aromatic-cationic peptide is reduced compared to the level of intermediate monocytes observed in step (a). In a further embodiment, the level of non-classical monocytes (CD14$^{low}$CD16$^{high}$) in the biological sample following the administration of the aromatic-cationic peptide is increased compared to the level of non-classical monocytes observed in step (a).

In some embodiments, the monocytes are circulating monocytes. In other embodiments, the monocytes are extravasated from the bloodstream to other tissues.

In some embodiments, the disease or condition characterized by mitochondrial dysfunction is ischemia, stroke, renal injury, neurodegenerative disease, atherosclerosis, metabolic syndrome, acute myocardial infarction, heart failure, ischemia reperfusion, ureteral obstruction, diabetic nephropathy, diabetes, Leber's Heredity Optic Neuropathy (LHON), Dominant Optic Atrophy (DOA), Barth's syndrome, POLG disease, or Leigh's disease. In some embodiments, the neurodegenerative disease is Alzheimer's disease, Amyotrophic Lateral Sclerosis (ALS), Huntington's disease, Friedreich's ataxia or Multiple Sclerosis.

In another embodiment, the present technology provides a method for evaluating the therapeutic efficacy of an aromatic-cationic peptide on a disease or condition characterized by mitochondrial dysfunction in a subject, comprising (a) assaying the ratio of different monocyte types present in a biological sample obtained from the subject, and (b) comparing the ratio of different monocyte types observed in step (a) with the ratio of corresponding monocyte types observed in a biological sample obtained from the subject following administration of a dose of an aromatic-cationic peptide, wherein the aromatic-cationic peptide is identified as having a therapeutic effect on the disease or condition characterized by mitochondrial dysfunction if the ratio of different monocyte types in the biological sample following the administration of the aromatic-cationic peptide is altered compared to the ratio of different monocyte types observed in step (a).

In some embodiments, the monocytes are circulating monocytes. In other embodiments, the monocytes are extravasated from the bloodstream to other tissues.

In some embodiments, the ratio of activated monocytes to non-classical monocytes in the biological sample following the administration of the aromatic-cationic peptide is reduced compared to the ratio of activated monocytes to non-classical monocytes observed in step (a). In some embodiments, the ratio of classical monocytes to non-classical monocytes in the biological sample following the administration of the aromatic-cationic peptide is reduced compared to the ratio of classical monocytes to non-classical monocytes observed in step (a). In some embodiments, the ratio of intermediate monocytes to non-classical monocytes in the biological sample following the administration of the aromatic-cationic peptide is reduced compared to the ratio of intermediate monocytes to non-classical monocytes observed in step (a).

In some embodiments, the ratio of classical monocytes to intermediate monocytes in the biological sample following the administration of the aromatic-cationic peptide is reduced compared to the ratio of classical monocytes to intermediate monocytes observed in step (a).

In some embodiments, the disease or condition characterized by mitochondrial dysfunction is ischemia, stroke, renal injury, neurodegenerative disease, atherosclerosis, metabolic syndrome, acute myocardial infarction, heart failure, ischemia reperfusion, ureteral obstruction, diabetic nephropathy, diabetes, Leber's Heredity Optic Neuropathy (LHON), Dominant Optic Atrophy (DOA), Barth's syndrome, POLG disease, or Leigh's disease. In some embodiments, the neurodegenerative disease is Alzheimer's disease, Amyotrophic Lateral Sclerosis (ALS), Huntington's disease, Friedreich's ataxia or Multiple Sclerosis.

In another embodiment, the present technology provides a method for evaluating the therapeutic efficacy of an aromatic-cationic peptide on a disease or condition characterized by mitochondrial dysfunction in a subject, comprising (a) assaying at least one biomarker of mitochondrial physiology of a population of monocytes present in a biological sample obtained from the subject, and (b) comparing the biomarker of mitochondrial physiology of the population of monocytes observed in step (a) with the biomarker of mitochondrial physiology of a corresponding population of monocytes observed in a biological sample obtained from the subject following administration of a dose of an aromatic-cationic peptide, wherein the aromatic-cationic peptide is identified as having a therapeutic effect on the disease or condition characterized by mitochondrial dysfunction if the biomarker of mitochondrial physiology of the population of monocytes in the biological sample following the administration of the aromatic-cationic peptide is similar to the biomarker of mitochondrial physiology of a corresponding population of monocytes in a reference sample. In some embodiments, the reference sample is a biological sample obtained from a healthy subject.

In some embodiments, the aromatic-cationic peptide is Phe-D-Arg-Phe-Lys-NH$_2$ or D-Arg-2'6'Dmt-Lys-Phe-NH$_2$ or a pharmaceutically acceptable salt thereof. In some embodiments, the monocytes are circulating monocytes. In other embodiments, the monocytes are extravasated from the bloodstream to other tissues.

In some embodiments, alterations in the biomarkers of mitochondrial physiology of monocytes can be determined using assays that measure disruption in oxidative phosphorylation. In some embodiments, disruption in oxidative phosphorylation is determined using assays that measure CoQ10 levels, uncoupling ratio, net routine flux control ratio, leak flux control ratio or phosphorylation respiratory control ratio. In some embodiments, alterations in the biomarkers of mitochondrial physiology of monocytes can be determined by measuring alterations in the levels of one or more biomarkers of mitochondrial physiology in a sample of monocytes. In some embodiments, biomarkers of mitochondrial physiology are selected from the group consisting of consisting of lactic acid (lactate) levels, pyruvic acid (pyruvate) levels, lactate/pyruvate ratios, phosphocreatine levels, NADH (NADH+H$^{30}$) or NADPH (NADPH+H$^{30}$) levels; NAD or NADP levels; ATP levels; reduced coenzyme Q (CoQred) levels; oxidized coenzyme Q (CoQox) levels; total coenzyme Q (CoQtot) levels; oxidized cytochrome C levels; reduced cytochrome C levels; oxidized cytochrome C/reduced cytochrome C ratio; acetoacetate levels; beta-hydroxy butyrate levels; acetoacetate/beta-hydroxy butyrate ratio; 8-hydroxy-2'-deoxyguanosine (8-OHdG) levels; levels of reactive oxygen species; oxygen consumption (VO2), carbon dioxide output (VCO2), and respiratory quotient (VCO2/VO2).

In some embodiments, the disease or condition characterized by mitochondrial dysfunction is ischemia, stroke, renal injury, neurodegenerative disease, atherosclerosis, metabolic syndrome, acute myocardial infarction, heart failure, ischemia reperfusion, ureteral obstruction, diabetic nephropathy, diabetes, Leber's Heredity Optic Neuropathy (LHON), Dominant Optic Atrophy (DOA), Barth's syndrome, POLG disease, or Leigh's disease. In some embodiments, the neurodegenerative disease is Alzheimer's disease, Amyotrophic Lateral Sclerosis (ALS), Huntington's disease, Friedreich's ataxia or Multiple Sclerosis.

In some embodiments, alterations in the biomarkers of mitochondrial physiology are determined using high throughput bioenergetics platforms.

BRIEF DESCRIPTION OF THE DRAWINGS

FIG. 1A shows the effect of D-Arg-2'6'Dmt-Lys-Phe-NH$_2$ on parameters of monocyte mitochondrial function over time. FIG. 1B shows the effect of saline on parameters of monocyte mitochondrial function over time. FIG. 1C shows a comparison of ATP production, maximal respiration, and respiratory capacity between the saline and D-Arg-2'6'Dmt-Lys-Phe-NH$_2$ treatment groups. Dogs with induced heart failure received a single 4-hour intravenous infusion of saline or D-Arg-2'6'Dmt-Lys-Phe-NH$_2$.

FIG. 2 illustrates the effect that various dysfunctions can have on biochemistry and biomarkers of mitochondrial physiology. It also indicates the physical effect (such as a disease symptom or other effect of the dysfunction) typically associated with a given dysfunction. It should be noted that any of the biomarkers of mitochondrial physiology listed in the figure, in addition to biomarkers of mitochondrial physiology enumerated elsewhere, can also be used to detect modulation, enhancement, or normalization by the compositions of the present technology in a sample of monocytes. RQ=respiratory quotient; BMR=basal metabolic rate; HR (CO)=heart rate (cardiac output); T=body temperature (preferably measured as core temperature); AT=anaerobic threshold; pH=blood pH venous and/or arterial).

DETAILED DESCRIPTION

General

It is to be appreciated that certain aspects, modes, embodiments, variations and features of the present technology are described below in various levels of detail in order to provide a substantial understanding of the present technology.

While the aromatic-cationic peptides described herein can occur and can be used as the neutral (non-salt) peptide, the description is intended to embrace all salts of the peptide described herein, as well as methods of using such salts of the peptides. In one embodiment, the salts of the aromatic-cationic peptides comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic peptide may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic peptides with amino acids, such as aspartate salts and glutamate salts, can also be prepared. The desired salt of an acidic peptide can be prepared by methods known to those of skill in the art by treating the compound with a base. Examples of inorganic salts of acidic peptides include, but are not limited to, alkali metal and alkaline earth salts, such as sodium salts, potassium salts, magnesium salts, and calcium salts; ammonium salts; and aluminum salts. Examples of organic salts of acidic peptides include, but are not limited to, procaine, dibenzylamine, N-ethylpiperidine, N,N'-dibenzylethylenediamine, and triethylamine salts. Salts of acidic peptides with amino acids, such as lysine salts, can also be prepared. The present technology also includes all stereoisomers and geometric isomers of the peptides of the present technology, including diastereomers, enantiomers, and cis/trans (E/Z) isomers. The present technology also includes mixtures of stereoisomers and/or geometric isomers in any ratio, including, but not limited to, racemic mixtures.

I Definitions

The definitions of certain terms as used in this specification are provided below. Unless defined otherwise, all technical and scientific terms used herein generally have the same meaning as commonly understood by one of ordinary skill in the art to which this present technology belongs.

As used in this specification and the appended claims, the singular forms "a", "an" and "the" include plural referents unless the content clearly dictates otherwise. For example, reference to "a cell" includes a combination of two or more cells, and the like.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs are compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics are chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "biological sample" refers to a sample from the subject, and includes any bodily fluids, exudates, tissues or cells. Non-limiting examples include blood, plasma, serum, urine, tears, sputum, stool, saliva, nasal swabs, cells such as, but not limited to peripheral blood mononuclear cells (PBMCs), leukocytes, and tissue samples (e.g., biopsy samples). Samples can be fresh, frozen, or otherwise treated or preserved for evaluation by the methods disclosed herein. In some embodiments, levels and mitochondrial physiological activity of monocytes are determined by assaying a biological sample from a subject using techniques that are well-known in the art.

As used herein, the term "biomarkers of mitochondrial physiology" refers to one or more physiological parameters that can be used to assess the frequency, output and regulation of distinct chemical and/or physical processes occurring within the mitochondria of monocytes and are selected from the group consisting of lactic acid (lactate) levels, pyruvic acid (pyruvate) levels, lactate/pyruvate ratios, phosphocreatine levels, NADH (NADH+H$^{30}$) or NADPH (NADPH+H$^{30}$) levels; NAD or NADP levels; ATP levels; reduced coenzyme Q (CoQred) levels; oxidized coenzyme Q (CoQox) levels; total coenzyme Q (CoQtot) levels; oxidized cytochrome C levels; reduced cytochrome C levels; oxidized cytochrome C/reduced cytochrome C ratio; acetoacetate levels; beta-hydroxy butyrate levels; acetoacetate/beta-hydroxy butyrate ratio; 8-hydroxy-2'-deoxyguanosine (8-OHdG) levels; levels of reactive oxygen species; oxygen consumption (VO2), carbon dioxide output (VCO2), respiratory quotient (VCO2/VO2) and any additional physiological parameters assessed by high resolution respirometry (e.g., Oxygraph-2k (OROBOROS)) and high throughput bioenergetics platforms such as XF Analyzers (Scahorse Biosciences).

The terms "circulating blood" or 'whole blood', which are used as equivalents herein, refer to the blood within the closed cardiovascular system of vertebrates. This comprises the blood in arteries (arterial blood), in veins (venous blood) as well as capillaries, venules and portal systems. Circulating blood cells are the cellular components of blood, consisting of red blood cells, white blood cells, and platelets, which are found within the circulating pool of blood and not sequestered within the lymphatic system, spleen, liver, or bone marrow. The term 'whole blood' encompasses both peripheral blood, found in the systemic circulation, and central blood, present in the pulmonary and coronary circulation.

The term "circulating monocytes" refers to monocytes that are present in the (peripheral or central) blood and thus part of the circulation (and not migrated into tissue). A "sample of monocytes" as used herein refers to a sample wherein the majority of cells are monocytes. In certain embodiments, the sample consists essentially of monocytes, or it consists exclusively of monocytes. Since only monocytes give rise to macrophages or dendritic cells (the myeloid lineage), and it is desirable that the sample represents this lineage, it is particularly envisaged that the sample contains as little other blood cells as feasible. Thus, it is envisaged that no (or virtually none, or as little as feasible) other leukocytes are present in the sample, that no (or virtually none, or as little as feasible) granulocytes are present in the sample, that no (or virtually none, or as little as feasible) other PBMCs are present in the sample, that no (or virtually none, or as little as feasible) lymphocytes (T cells, B cells, NK cells) are present in the sample.

According to particular embodiments, the sample does not consist of a mixed monocyte-lymphocyte population. In other words, the sample is not a population of peripheral blood mononuclear cells. According to alternative embodiments, the sample does not contain lymphocytes. Thus, a sample of monocytes can be interpreted as a sample of isolated monocytes. In other words, although circulating blood contains monocytes, according to particular embodiments, it does not fulfill the definition of a sample of monocytes. In some embodiments, to obtain a sample of monocytes from a blood sample, a further separation or isolation step is needed. Typically, by way of example but not by way of limitation, this is done by density gradient separation (to isolate the PBMC from the rest of the blood constituents) followed by marker-assisted separation; but a one-step isolation procedure (by marker(s) only) can be applied as well. For example, in humans, one can separate the CD14-expressing cells in peripheral blood from the non-CD14-expressing cells to obtain a sample of monocytes as envisaged herein. Monocytes can be further divided into subpopulations, for instance depending on expression of particular receptors (e.g., but not limited to, CD16).

As used herein, the term "effective amount" refers to a quantity sufficient to achieve a desired therapeutic and/or prophylactic effect, e.g., an amount which results in the prevention of, or a decrease in a disease or condition or one or more symptoms associated with a disease or condition characterized by mitochondrial dysfunction. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. As discussed herein, active agents such as aromatic-cationic peptide compositions can also be administered in combination with one or more additional therapeutic compounds. In the methods described herein, the active agents (e.g., an aromatic-cationic peptide) may be administered to a subject having one or more signs or symptoms of a disease or condition characterized by mitochondrial dysfunction. For example, a "therapeutically effective amount" of the active agents (e.g., an aromatic-cationic peptide) is meant levels in which the physiological effects of a disease or condition characterized by mitochondrial dysfunction are, at a minimum, ameliorated. A therapeutically effective amount can be given in one or more administrations. Tn some embodiments, signs, symptoms or complications of a disease or condition characterized by mitochondrial dysfunction include, but are not limited to: increased levels of activated monocytes, poor growth, loss of muscle coordination, muscle weakness, neurological deficit, seizures, autism, autistic spectrum, autistic-like features, learning disabilities, heart disease, liver disease, kidney disease, gastrointestinal disorders, severe constipation, diabetes, increased risk of infection, thyroid dysfunction, adrenal dysfunction, autonomic dysfunction, confusion, disorientation, memory loss, failure to thrive, poor coordination, sensory (vision, hearing) problems, reduced mental functions, disease of the organ, dementia, respiratory problems, hypoglycemia, apnea, lactic acidosis, seizures, swallowing difficulties, developmental delays, movement disorders (dystonia, muscle spasms, tremors, chorea), stroke, and brain atrophy. In some embodiments, an "effective amount" of a compound is an amount of the compound sufficient to modulate, normalize, or enhance one or more biomarkers of mitochondrial physiology (where modulation, normalization, and enhancement are defined below) in cells, such as monocytes.

As used herein, "enhancement" of, or to "enhance," biomarkers of mitochondrial physiology means to intentionally change the level of one or more biomarkers of mitochondrial physiology in cells, such as monocytes, that are present in a biological sample away from either the normal value, or the value before enhancement, in order to achieve a beneficial or desired effect. For example, enhancement can be of beneficial effect in a subject suffering from a disease or condition characterized by mitochondrial dysfunction, in that normalizing a biomarker of mitochondrial physiology may not achieve the optimum outcome for the subject; in such cases, enhancement of one or more biomarkers of mitochondrial physiology can be beneficial, for example, higher-than-normal levels of ATP, or lower-than normal levels of lactic acid (lactate) can be beneficial to such a subject.

As used herein, the term "heart failure" encompasses all forms of heart failure, including but not limited to, e.g., "congestive heart failure" (CHF), "chronic heart failure," and "acute heart failure." As used herein, the term encompasses both sporadic and genetic forms of heart failure. As is known in the art, heart failure is typically characterized by abnormally low cardiac output in which the heart is unable to pump blood at an adequate rate or in adequate volume. When the heart is unable to adequately pump blood to the rest of the body, or when one or more of the heart valves becomes stenotic or otherwise incompetent, blood can back up into the lungs, causing the lungs to become congested with fluid. If this backward flow occurs over an extended period of time, heart failure can result. Typical symptoms of heart failure include shortness of breath (dyspnea), fatigue, weakness, difficulty breathing when lying flat, and swelling of the legs, ankles or abdomen (edema). Causes of heart failure may be related to various disorders including coronary artery disease, systemic hypertension, cardiomyopathy or myocarditis, congenital heart disease, abnormal heart valves or valvular heart disease, severe lung disease, diabetes, severe anemia hyperthyroidism, arrhythmia or dysrhythmia and myocardial infarction. The primary signs of congestive heart failure are cardiomegaly (enlarged heart), tachypnea (rapid breathing; occurs in the case of left side failure) and hepatomegaly (enlarged liver; occurs in the case of right side failure).

As used herein, the term "hypertensive cardiomyopathy" refers to a condition characterized by a weakened heart caused by the effects of hypertension (high blood pressure). Over time, uncontrolled hypertension causes weakness of the heart muscle. As hypertensive cardiomyopathy worsens, it can lead to congestive heart failure. Early symptoms of hypertensive cardiomyopathy include cough, weakness, and fatigue. Additional symptoms of hypertensive cardiomyopathy include leg swelling, weight gain, difficulty breathing when lying flat, increasing shortness of breath with activity, and waking in the middle of the night short of breath.

As used herein, the term "ischemia" refers to a decrease in the blood supply to the tissue and is followed by "reperfusion," a sudden perfusion of oxygen into the deprived tissue.

As used herein, an "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, the term "disease or condition characterized by mitochondrial dysfunction" refers to a disease or condition selected from the group consisting of ischemia, stroke, renal injury, neurodegenerative disease, atherosclerosis, metabolic syndrome, acute myocardial infarction, heart failure, ischemia reperfusion, ureteral obstruction, diabetic nephropathy, diabetes, Leber's Heredity Optic Neuropathy (LHON), Dominant Optic Atrophy (DOA), Barth's syndrome, POLG disease, or Leigh's disease. In some embodiments, the neurodegenerative disease is Alzheimer's disease, Amyotrophic Lateral Sclerosis (ALS), Huntington's disease, Friedreich's ataxia or Multiple Sclerosis. In some embodiments, the disease or condition characterized by mitochondrial dysfunction manifests as a result of genetic factors. In other embodiments, the disease or condition characterized by mitochondrial dysfunction is induced by non-genetic factors.

The term "monocytes" as used herein refers to a particular type of white blood cells (leukocytes) that are part of the innate immune system of vertebrates. Monocytes are normally produced by the bone marrow from hematopoietic stem cell precursors called monoblasts. They circulate in the bloodstream for about one to three days and then typically move into tissues throughout the body. Monocytes constitute between three to eight percent of the leukocytes in the blood (reference values in healthy adult humans), and are the largest corpuscle in blood. Once extravasated from the bloodstream to other tissues, they will differentiate into tissue resident macrophages or dendritic cells. Monocytes play multiple roles in immune function such as: (1) replenishing resident macrophages under normal states, and (2) rapidly migrating to sites of infection or metabolic stress in tissues in response to inflammation signals. There are at least three types of monocytes in human blood: a) the classical monocyte, which is characterized by high level expression of the CD14 cell surface receptor ($CD14^{++}$ $CD16^-$ monocyte), b) the non-classical monocyte, which shows low level expression of CD14 and high level expression of the CD16 receptor ($CD14^+CD16^{++}$ monocyte), and c) the intermediate monocyte with high level expression of CD14 and low level expression of CD16 ($CD14^{++}CD16^+$ monocytes). In humans, CD14 is considered a marker of the monocyte lineage. So, at least in humans, 'monocytes' can be considered equivalent to CD14-expressing cells that circulate in the bloodstream (the latter property distinguishing them from dendritic cells and macrophages). Although virtually all CD14-expressing cells in peripheral blood will be monocytes, further differentiation using other markers or cell size can be made to distinguish monocytes from other cell types.

As used herein, the "modulation" of, or to "modulate," a biomarker of mitochondrial physiology means to change the level of the biomarker of mitochondrial physiology in monocytes that are present in a biological sample towards a desired value, or to change the level of the biomarker of mitochondrial physiology in a desired direction (e.g., increase or decrease). Modulation can include, but is not limited to, normalization and enhancement as defined herein.

As used herein, the term "net charge" refers to the balance of the number of positive charges and the number of negative charges carried by the amino acids present in the aromatic-cationic peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

As used herein, "normalization" of, or to "normalize," a biomarker of mitochondrial physiology means changing the level of the biomarker of mitochondrial physiology in cells, such as monocytes, that are present in a biological sample, from a pathological value towards a normal value, where the normal value of the biomarker of mitochondrial physiology can be 1) the level of the biomarker of mitochondrial physiology in a healthy person or subject, or 2) a level of the biomarker of mitochondrial physiology that alleviates one or more undesirable symptoms in the person or subject. That is, to normalize a biomarker of mitochondrial physiology which is depressed in a disease state means to increase the level of the biomarker of mitochondrial physiology towards the normal (healthy) value or towards a value which alleviates an undesirable symptom; to normalize a biomarker of mitochondrial physiology which is elevated in a disease state means to decrease the level of the biomarker of mitochondrial physiology towards the normal (healthy) value or towards a value which alleviates an undesirable symptom.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, "preventing" or "prevention" of a disease or condition characterized by mitochondrial dysfunction refers to one or more compounds that, in a statistical sample, reduces the occurrence of the disorder or condition in the treated sample relative to an untreated control sample, or delays the onset or reduces the severity of one or more symptoms of the disorder or condition relative to the untreated control sample. As used herein, preventing a disease or condition characterized by mitochondrial dysfunction includes preventing oxidative damage or preventing mitochondrial permeability transitioning, thereby preventing or ameliorating the harmful effects of the disruption of mitochondrial oxidative phosphorylation.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, the terms "subject," "individual," or "patient" can be an individual organism, a vertebrate, a mammal, or a human.

A "synergistic therapeutic effect" refers to a greater-than-additive therapeutic effect which is produced by a combination of at least two therapeutic agents, and which exceeds that which would otherwise result from individual administration of the therapeutic agents alone. For example, lower doses of one or both of the therapeutic agents may be used in treating a disease, resulting in increased therapeutic efficacy and decreased side-effects.

As used herein, the term "therapeutic use" of the compounds discussed herein is defined as using one or more of the active agents discussed herein to treat or suppress a disease, as defined herein.

As used herein, the term "transient ischemic attack (TIA)" refers to periods when blood flow to a part of the brain is interrupted for a brief period of time. TIAs last from a few minutes to 1-2 hours, and may occur again at a later time. The symptoms of TIA are the same as the symptoms of a stroke, and include sudden vertigo or dizziness, sudden changes in alertness, sudden changes in sensory perception (including touch, pain, temperature, pressure, hearing, and taste), memory loss, difficulty swallowing, drooping of the face, inability to recognize objects or people, lack of bladder or bowel control, lack of coordination, loss of vision in one or both eyes, weakness, numbness or tingling on one side of the body etc.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. For example, a subject is successfully "treated" for a disease or disorder characterized by mitochondrial dysfunction if, after receiving a therapeutic amount of the active agents (e.g., an aromatic-cationic peptide) according to the methods described herein, the subject shows observable and/or measurable reduction in the disruption of mitochondrial oxidative phosphorylation. It is also to be appreciated that the various modes of treatment or prevention of medical diseases and conditions as described are intended to mean "substantial," which includes total but also less than total treatment or prevention, and wherein some biologically or medically relevant result is achieved.

II Aromatic-Cationic Peptides of the Present Technology

The aromatic-cationic peptides of the present technology are water-soluble and highly polar. Despite these properties, the peptides can readily penetrate cell membranes. The aromatic-cationic peptides typically include a minimum of three amino acids or a minimum of four amino acids, covalently joined by peptide bonds. The maximum number of amino acids present in the aromatic-cationic peptides is about twenty amino acids covalently joined by peptide bonds. Suitably, the maximum number of amino acids is about twelve, or about nine, or about six.

In some aspects, the present technology provides an aromatic-cationic peptide or a pharmaceutically acceptable salt thereof such as acetate salt or trifluoroacetate salt. In some embodiments, the peptide comprises at least one net positive charge; a minimum of three amino acids; a maximum of about twenty amino acids;

a relationship between the minimum number of net positive charges ($p_m$) and the total number of amino acid residues (r) wherein $3p_m$ is the largest number that is less than or equal to r+1; and a relationship between the minimum number of aromatic groups (a) and the total number of net positive charges ($p_t$) wherein 2a is the largest number that is less than or equal to $p_t+1$, except that when a is 1, $p_t$ may also be 1.

In some embodiments, the peptide comprises the amino acid sequence Phe-D-Arg-Phe-Lys-$NH_2$ or D-Arg-2'6'-Dmt-Lys-Phe-$NH_2$. In some embodiments, the peptide comprises one or more of the peptides of Table A:

TABLE A

Phe-Arg-D-His-Asp
Met-Tyr-D-Lys-Phe-Arg
Phe-D-Arg-His
Tyr-D-Arg-Phe-Lys-$NH_2$
2'6'-Dmt-D-Arg-Phe-Lys-$NH_2$
2'6'-Dmt-D-Arg-Phe Orn-$NH_2$
2'6'-Dmt-D-Cit-Phe Lys-$NH_2$
Phe-D-Arg-2'6'-Dmt-Lys-$NH_2$
2'6'-Dmt-D-Arg-Phe-Ahp-$NH_2$
H-Phe-D-Arg-Phe-Lys-Cys-$NH_2$
2'6'-Dmp-D-Arg-2'6'-Dmt-Lys-$NH_2$
2'6'-Dmp-D-Arg-Phe-Lys-$NH_2$
Tyr-Arg-Phe-Lys-Glu-His-Trp-D-Arg
Lys-Gln-Tyr-D-Arg-Phe-Trp
D-Arg-2'6'-Dmt-Lys-Trp-$NH_2$

TABLE A-continued

```
D-Arg-Trp-Lys-Trp-NH₂
D-Arg-2'6'-Dmt-Lys-Phe-Met-NH₂
D-Arg-2'6'-Dmt-Lys(NαMe)-Phe-NH₂
D-Arg-2'6'-Dmt-Lys-Phe(NMe)-NH₂
D-Arg-2'6'-Dmt-Lys(NαMe)-Phe(NMe)-NH₂
D-Arg(NαMe)-2'6'-Dmt(NMe)-Lys(NαMe)-Phe(NMe)-NH₂
D-Arg-2'6'-Dmt-Lys-Phe-Lys-Trp-NH₂
D-Arg-2'6'-Dmt-Lys-2'6'-Dmt-Lys-Trp-NH₂
D-Arg-2'6'-Dmt-Lys-Phe-Lys-Met-NH₂
D-Arg-2'6'-Dmt-Lys-2'6'-Dmt-Lys-Met-NH₂
D-Arg-2'6'-Dmt-Lys-Phe-Sar-Gly-Cys-NH₂
D-Arg-Ψ[CH₂—NH]2'6'-Dmt-Lys-Phe-NH₂
D-Arg-2'6'-Dmt-Ψ[CH₂—NH]Lys-Phe-NH₂
D-Arg-2'6'-Dmt-LysΨ[CH₂—NH]Phe-NH₂
D-Arg-2'6'-Dmt-Ψ[CH₂—NH]Lys-Ψ[CH₂—NH]Phe-NH₂
Lys-D-Arg-Tyr-NH₂
D-Tyr-Trp-Lys-NH₂
Trp-D-Lys-Tyr-Arg-NH₂
Tyr-His-D-Gly-Met
Tyr-D-Arg-Phe-Lys-Glu-NH₂
Met-Tyr-D-Arg-Phe-Arg-NH₂
D-His-Glu-Lys-Tyr-D-Phe-Arg
Lys-D-Gln-Tyr-Arg-D-Phe-Trp-NH₂
Phe-D-Arg-Lys-Trp-Tyr-D-Arg-His
Gly-D-Phe-Lys-His-D-Arg-Tyr-NH₂
Val-D-Lys-His-Tyr-D-Phe-Ser-Tyr-Arg-NH₂
Trp-Lys-Phe-D-Asp-Arg-Tyr-D-His-Lys
Lys-Trp-D-Tyr-Arg-Asn-Phe-Tyr-D-His-NH₂
Thr-Gly-Tyr-Arg-D-His-Phe-Trp-D-His-Lys
Asp-D-Trp-Lys-Tyr-D-His-Phe-Arg-D-Gly-Lys-NH₂
D-His-Lys-Tyr-D-Phe-Glu-D-Asp-D-Asp-D-His-D-Lys-Arg-Trp-NH₂
Ala-D-Phe-D-Arg-Tyr-Lys-D-Trp-His-D-Tyr-Gly-Phe
Tyr-D-His-Phe-D-Arg-Asp-Lys-D-Arg-His-Trp-D-His-Phe
Phe-Phe-D-Tyr-Arg-Glu-Asp-D-Lys-Arg-D-Arg-His-Phe-NH₂
Phe-Tyr-Lys-D-Arg-Trp-His-D-Lys-D-Lys-Glu-Arg-D-Tyr-Thr
Tyr-Asp-D-Lys-Tyr-Phe-D-Lys-D-Arg-Phe-Pro-D-Tyr-His-Lys
Glu-Arg-D-Lys-Tyr-D-Val-Phe-D-His-Trp-Arg-D-Gly-Tyr-Arg-D-Met-NH₂
Arg-D-Leu-D-Tyr-Phe-Lys-Glu-D-Lys-Arg-D-Trp-Lys-D-Phe-Tyr-D-Arg-Gly
D-Glu-Asp-Lys-D-Arg-D-His-Phe-Phe-D-Val-Tyr-Arg-Tyr-D-Tyr-Arg-His-Phe-NH₂
Asp-Arg-D-Phe-Cys-Phe-D-Arg-D-Lys-Tyr-Arg-D-Tyr-Trp-D-His-Tyr-D-Phe-Lys-Phe
His-Tyr-D-Arg-Trp-Lys-Phe-D-Asp-Ala-Arg-Cys-D-Tyr-His-Phe-D-Lys-Tyr-His-Ser-NH₂
Gly-Ala-Lys-Phe-D-Lys-Glu-Arg-Tyr-His-D-Arg-D-Arg-Asp-Tyr-Trp-D-His-Trp-His-D-Lys-Asp
Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH₂
```

2',6'-dimethyltyrosine (2'6'-Dmt); dimethyltyrosine (Dmt)

In one embodiment, the aromatic-cationic peptide is defined by Formula A:

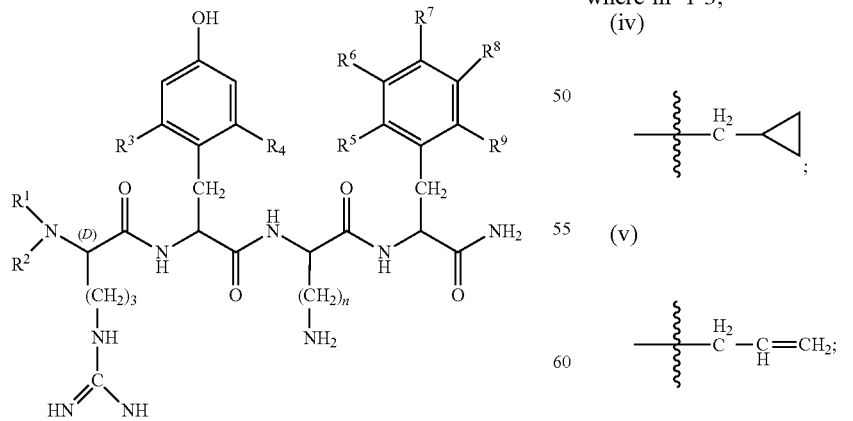

wherein $R^1$ and $R^2$ are each independently selected from
(i) hydrogen;
(ii) linear or branched $C_1$-$C_6$ alkyl;

(iii)

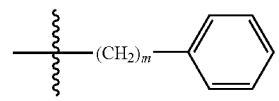

where m=1-3;

(iv)

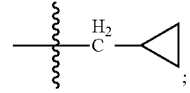 [SMILES: *CC1CC1]

(v)

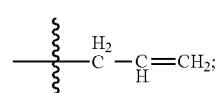

$R^3$ and $R^4$ are each independently selected from
(i) hydrogen;
(ii) linear or branched $C_1$-$C_6$ alkyl;
(iii) $C_1$-$C_6$ alkoxy;
(iv) amino;

(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo;

$R^5$, $R^6$, $R^7$, $R^8$, and $R^9$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and n is an integer from 1 to 5.

In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

In one embodiment, the peptide is defined by Formula B:

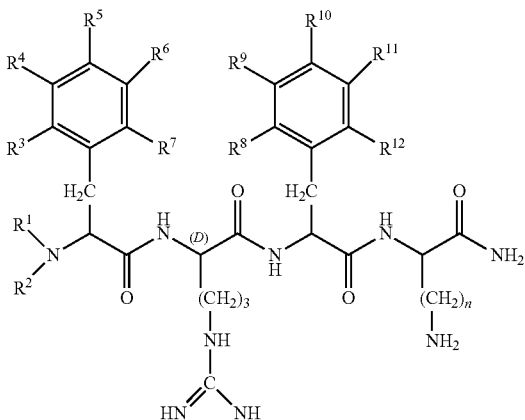

wherein $R^1$ and $R^2$ are each independently selected from
(i) hydrogen;
(ii) linear or branched $C_1$-$C_6$ alkyl;
(iii)

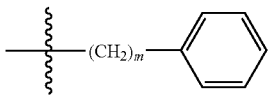

where m=1-3;
(iv)

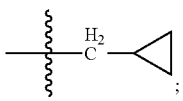 [SMILES: *CC1CC1]

(v)

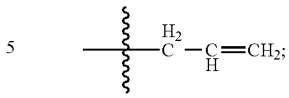

$R^3$, $R^4$, $R^5$, $R^6$, $R^7$, $R^8$, $R^9$, $R^{10}$, $R^{11}$ and $R^{12}$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and n is an integer from 1 to 5.

In a particular embodiment, $R^1$, $R^2$, $R^3$, $R^4$, $R^5$, $R^6$, $R^7$, $R^8$, $R^9$, $R^{10}$, $R^{11}$, and $R^{12}$ are all hydrogen; and n is 4. In another embodiment, $R^1$, $R^2$, $R^3$, $R^4$, $R^5$, $R^6$, $R^7$, $R^9$, and $R^{11}$ are all hydrogen; $R^8$ and $R^{12}$ are methyl; $R^{10}$ is hydroxyl; and n is 4.

In one embodiment, the aromatic-cationic peptides of the present technology have a core structural motif of alternating aromatic and cationic amino acids. For example, the peptide may be a tetrapeptide defined by any of Formulas C to F set forth below:

| | |
|---|---|
| Aromatic-Cationic-Aromatic-Cationic | (Formula C) |
| Cationic-Aromatic-Cationic-Aromatic | (Formula D) |
| Aromatic-Aromatic-Cationic-Cationic | (Formula E) |
| Cationic-Cationic-Aromatic-Aromatic | (Formula F) | wherein, aromatic is a residue selected from the group consisting of: Phe (F), Tyr (Y), Trp (W), and Cyclohexylalanine (Cha); and Cationic is a residue selected from the group consisting of: Arg (R), Lys (K), Norleucine (Nle), and 2-amino-heptanoic acid (Ahe).

The peptides disclosed herein may be formulated as pharmaceutically acceptable salts. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the salt is an acetate salt. Additionally or alternatively, in other embodiments, the salt is a trifluoroacetate salt.

The aromatic-cationic peptides of the present technology disclosed herein may be synthesized by any of the methods well known in the art. Suitable methods for chemically synthesizing the protein include, for example, liquid phase and solid phase synthesis, and those methods described by Stuart and Young in *Solid Phase Peptide Synthesis*, Second Edition, Pierce Chemical Company (1984), and in *Methods Enzymol.*, 289, Academic Press, Inc, New York (1997). Recombinant peptides may be generated using conventional techniques in molecular biology, protein biochemistry, cell biology, and microbiology, such as those described in *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, Meth. Enzymol., (Academic Press, Inc., 1984); *Gene Transfer Vectors for Mammalian Cells*, Miller & Calos, Eds. (Cold Spring Harbor Laboratory, NY, 1987); and Meth. Enzymol., Vols. 154 and 155, Wu & Grossman, and Wu, Eds., respectively.

Aromatic-cationic peptide precursors may be made by either chemical (e.g., using solution and solid phase chemical peptide synthesis) or recombinant syntheses known in the art. Precursors of e.g., amidated aromatic-cationic peptides of the present technology may be made in like manner. In some embodiments, recombinant production is believed significantly more cost effective. In some embodiments, precursors are converted to active peptides by amidation reactions that are also known in the art. For example, enzymatic amidation is described in U.S. Pat. No. 4,708,934 and European Patent Publications 0 308 067 and 0 382 403. Recombinant production can be used for both the precursor and the enzyme that catalyzes the conversion of the precursor to the desired active form of the aromatic-cationic peptide. Such recombinant production is discussed in Biotechnology, Vol. 11 (1993) pp. 64-70, which further describes a conversion of a precursor to an amidated product. During amidation, a keto-acid such as an alpha-keto acid, or salt or ester thereof, wherein the alpha-keto acid has the molecular structure RC(O)C(O)OH, and wherein R is selected from the group consisting of aryl, a $C_1$-$C_4$ hydrocarbon moiety, a halogenated or hydroxylated $C_1$-$C_4$ hydrocarbon moiety, and a $C_1$-$C_4$ carboxylic acid, may be used in place of a catalase co-factor. Examples of these keto acids include, but are not limited to, ethyl pyruvate, pyruvic acid and salts thereof, methyl pyruvate, benzoyl formic acid and salts thereof, 2-ketobutyric acid and salts thereof, 3-methyl-2-oxobutanoic acid and salts thereof, and 2-keto glutaric acid and salts thereof.

In some embodiments, the production of the recombinant aromatic-cationic peptide may proceed, for example, by producing glycine-extended precursor in *E. coli* as a soluble fusion protein with glutathione-S-transferase. An a-amidating enzyme catalyzes conversion of precursors to active aromatic-cationic peptide. That enzyme is recombinantly produced, for example, in Chinese Hamster Ovary (CHO) cells as described in the Biotechnology article cited above. Other precursors to other amidated peptides may be produced in like manner. Peptides that do not require amidation or other additional functionalities may also be produced in like manner. Other peptide active agents are commercially available or may be produced by techniques known in the art.

The peptides optionally contain one or more non-naturally occurring amino acids. Optimally, the peptide has no amino acids that are naturally occurring. The non-naturally occurring amino acids may be levorotary (L-), dextrorotatory (D-), or mixtures thereof. Non-naturally occurring amino acids are those amino acids that typically are not synthesized in normal metabolic processes in living organisms, and do not naturally occur in proteins. In addition, the non-naturally occurring amino acids suitably are also not recognized by common proteases. The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include α-aminobutyric acid, β-aminobutyric acid, γ-aminobutyric acid, δ-aminovaleric acid, and ε-aminocaproic acid. Some examples of non-natural aryl amino acids include ortho-, meta, and para-aminobenzoic acid. Some examples of non-natural alkylaryl amino acids include ortho-, meta-, and para-aminophenylacetic acid, and γ-phenyl-β-aminobutyric acid. Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2',3',4',5', or 6' position of the aromatic ring of a phenylalanine or tyrosine residue, or the 4',5',6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide is the derivatization of a carboxyl group of an aspartic acid or a glutamic acid residue of the peptide. One example of derivatization is amidation with ammonia or with a primary or secondary amine, e.g., methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are suitably resistant or insensitive to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides should have less than five, or less than four, or less than three, or less than two contiguous L-amino acids recognized by common proteases, irrespective of whether the amino acids are naturally or non-naturally occurring. Optimally, the peptide has only D-amino acids, and no L-amino acids. If the peptide contains protease sensitive sequences of amino acids, at least one of the amino acids is a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

The aromatic-cationic peptides should have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r). The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

Typically, a peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-D-Arg has one negatively charged amino acid (i.e., Glu) and four positively charged amino acids (i.e., two Arg residues, one Lys, and one His). Therefore, the above peptide has a net positive charge of three.

In one embodiment, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

TABLE 1

Amino acid number and net positive charges ($3p_m \le p + 1$)

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 2

Amino acid number and net positive charges ($2p_m \le p + 1$)

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, or a minimum of two net positive charges, or a minimum of three net positive charges.

It is also important that the aromatic-cationic peptides have a minimum number of aromatic groups in comparison to the total number of net positive charges ($p_t$). The minimum number of aromatic groups will be referred to below as (a). Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides should also have a relationship between the minimum number of aromatic groups (a) and the total number of net positive charges at physiological pH ($p_t$) wherein 3a is the largest number that is less than or equal to $p_t$+1, except that when $p_t$ is 1, a may also be 1. In this embodiment, the relationship between the minimum number of aromatic groups (a) and the total number of net positive charges ($p_t$) is as follows:

TABLE 3

Aromatic groups and net positive charges ($3a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t+1$. In this embodiment, the relationship between the minimum number of aromatic amino acid residues (a) and the total number of net positive charges ($p_t$) is as follows:

TABLE 4

Aromatic groups and net positive charges ($2a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, are suitably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group. The free carboxylate groups of the asparagine, glutamine, aspartic acid, and glutamic acid residues not occurring at the C-terminus of the aromatic-cationic peptides may also be amidated wherever they occur within the peptide. The amidation at these internal positions may be with ammonia or any of the primary or secondary amines described above.

In one embodiment, the aromatic-cationic peptide is a tripeptide having two net positive charges and at least one aromatic amino acid. In a particular embodiment, the aromatic-cationic peptide is a tripeptide having two net positive charges and two aromatic amino acids.

Aromatic-cationic peptides include, but are not limited to, the following peptide examples:

TABLE 5

EXEMPLARY PEPTIDES

2',6'-Dmp-D-Arg-2',6'-Dmt-Lys-NH$_2$
2',6'-Dmp-D-Arg-Phe-Lys-NH$_2$
2',6'-Dmt-D-Arg-PheOrn-NH$_2$
2',6'-Dmt-D-Arg-Phe-Ahp(2-aminoheptanoicacid)-NH$_2$
2',6'-Dmt-D-Arg-Phe-Lys-NH$_2$
2',6'-Dmt-D-Cit-PheLys-NH$_2$
Ala-D-Phe-D-Arg-Tyr-Lys-D-Trp-His-D-Tyr-Gly-Phe
Arg-D-Leu-D-Tyr-Phe-Lys-Glu-D-Lys-Arg-D-Trp-Lys-D-Phe-Tyr-D-Arg-Gly
Asp-Arg-D-Phe-Cys-Phe-D-Arg-D-Lys-Tyr-Arg-D-Tyr-Trp-D-His-Tyr-D-Phe-Lys-Phe
Asp-D-Trp-Lys-Tyr-D-His-Phe-Arg-D-Gly-Lys-NH$_2$
D-Arg-2',6'-Dmt-Lys-Phe-NH$_2$
D-Glu-Asp-Lys-D-Arg-D-His-Phe-Phe-D-Val-Tyr-Arg-Tyr-D-Tyr-Arg-His-Phe-NH$_2$
D-His-Glu-Lys-Tyr-D-Phe-Arg
D-His-Lys-Tyr-D-Phe-Glu-D-Asp-D-Asp-D-His-D-Lys-Arg-Trp-NH$_2$
D-Tyr-Trp-Lys-NH$_2$
Glu-Arg-D-Lys-Tyr-D-Val-Phe-D-His-Trp-Arg-D-Gly-Tyr-Arg-D-Met-NH$_2$
Gly-Ala-Lys-Phe-D-Lys-Glu-Arg-Tyr-His-D-Arg-D-Arg-Asp-Tyr-Trp-D-His-Trp-His-D-Lys-Asp.
Gly-D-Phe-Lys-His-D-Arg-Tyr-NH$_2$
His-Tyr-D-Arg-Trp-Lys-Phe-D-Asp-Ala-Arg-Cys-D-Tyr-His-Phe-D-Lys-Tyr-His-Ser-NH$_2$
Lys-D-Arg-Tyr-NH$_2$
Lys-D-Gln-Tyr-Arg-D-Phe-Trp-NH$_2$
Lys-Trp-D-Tyr-Arg-Asn-Phe-Tyr-D-His-NH$_2$
Met-Tyr-D-Arg-Phe-Arg-NH$_2$
Met-Tyr-D-Lys-Phe-Arg
Phe-Arg-D-His-Asp
Phe-D-Arg-2',6'-Dmt-Lys-NH$_2$
Phe-D-Arg-His
Phe-D-Arg-Lys-Trp-Tyr-D-Arg-His
Phe-D-Arg-Phe-Lys-NH$_2$
Phe-Phe-D-Tyr-Arg-Glu-Asp-D-Lys-Arg-D-Arg-His-Phe-NH$_2$
Phe-Tyr-Lys-D-Arg-Trp-His-D-Lys-D-Lys-Glu-Arg-D-Tyr-Thr
Thr-Gly-Tyr-Arg-D-His-Phe-Trp-D-His-Lys TABLE 5-continued

EXEMPLARY PEPTIDES

Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH$_2$
Trp-D-Lys-Tyr-Arg-NH$_2$
Trp-Lys-Phe-D-Asp-Arg-Tyr-D-His-Lys
Tyr-Asp-D-Lys-Tyr-Phe-D-Lys-D-Arg-Phe-Pro-D-Tyr-His-Lys
Tyr-D-Arg-Phe-Lys-Glu-NH$_2$
Tyr-D-Arg-Phe-Lys-NH$_2$
Tyr-D-His-Phe-D-Arg-Asp-Lys-D-Arg-His-Trp-D-His-Phe
Tyr-His-D-Gly-Met
Val-D-Lys-His-Tyr-D-Phe-Ser-Tyr-Arg-NH$_2$

In one embodiment, the peptides have mu-opioid receptor agonist activity (i.e., they activate the mu-opioid receptor). Peptides which have mu-opioid receptor agonist activity are typically those peptides which have a tyrosine residue or a tyrosine derivative at the N-terminus (i.e., the first amino acid position). Suitable derivatives of tyrosine include 2'-methyltyrosine (Mmt); 2',6'-dimethyltyrosine (2'6'-Dmt); 3',5'-dimethyltyrosine (3'5'Dmt); N,2',6'-trimethyltyrosine (Tmt); and 2'-hydroxy-6'-methyltyrosine (Hint).

In one embodiment, a peptide that has mu-opioid receptor agonist activity has the formula Tyr-D-Arg-Phe-Lys-NH$_2$. Tyr-D-Arg-Phe-Lys-NH$_2$ has a net positive charge of three, contributed by the amino acids tyrosine, arginine, and lysine and has two aromatic groups contributed by the amino acids phenylalanine and tyrosine. The tyrosine of Tyr-D-Arg-Phe-Lys-NH$_2$ can be a modified derivative of tyrosine such as in 2',6'-dimethyltyrosine to produce the compound having the formula 2',6'-Dmt-D-Arg-Phe-Lys-NH$_2$. 2',6'-Dmt-D-Arg-Phe-Lys-NH$_2$ has a molecular weight of 640 and carries a net three positive charge at physiological pH. 2',6'-Dmt-D-Arg-Phe-Lys-NH$_2$ readily penetrates the plasma membrane of several mammalian cell types in an energy-independent manner (Zhao et al., *J. Pharmacol Exp Ther.*, 304:425-432, 2003).

Alternatively, in other instances, the aromatic-cationic peptide does not have mu-opioid receptor agonist activity. For example, during long-term treatment, such as in a chronic disease state or condition, the use of an aromatic-cationic peptide that activates the mu-opioid receptor may be contraindicated. In these instances, the potentially adverse or addictive effects of the aromatic-cationic peptide may preclude the use of an aromatic-cationic peptide that activates the mu-opioid receptor in the treatment regimen of a human patient or other mammal. Potential adverse effects may include sedation, constipation and respiratory depression. In such instances an aromatic-cationic peptide that does not activate the mu-opioid receptor may be an appropriate treatment. Peptides that do not have mu-opioid receptor agonist activity generally do not have a tyrosine residue or a derivative of tyrosine at the N-terminus (i.e., amino acid position 1). The amino acid at the N-terminus can be any naturally occurring or non-naturally occurring amino acid other than tyrosine. In one embodiment, the amino acid at the N-terminus is phenylalanine or its derivative. Exemplary derivatives of phenylalanine include 2'-methylphenylalanine (Mmp), 2',6'-dimethylphenylalanine (2',6'-Dmp), N,2',6'-trimethylphenylalanine (Tmp), and 2'-hydroxy-6'-methylphenylalanine (Hmp).

An example of an aromatic-cationic peptide that does not have mu-opioid receptor agonist activity has the formula Phe-D-Arg-Phe-Lys-NH$_2$. Alternatively, the N-terminal phenylalanine can be a derivative of phenylalanine such as 2',6'-dimethylphenylalanine (2'6'-Dmp). In one embodiment, the amino acid sequence of 2',6'-Dmt-D-Arg-Phe-Lys-NH$_2$ is rearranged such that Dmt is not at the N-terminus. An example of such an aromatic-cationic peptide that does not have mu-opioid receptor agonist activity has the formula D-Arg-2'6'-Dmt-Lys-Phe-NH$_2$.

Suitable substitution variants of the peptides listed herein include conservative amino acid substitutions Amino acids may be grouped according to their physicochemical characteristics as follows:

(a) Non-polar amino acids: Ala(A) Ser(S) Thr(T) Pro(P) Gly(G) Cys (C);
(b) Acidic amino acids: Asn(N) Asp(D) Glu(E) Gln(Q);
(c) Basic amino acids: His(H) Arg(R) Lys(K);
(d) Hydrophobic amino acids: Met(M) Leu(L) Ile(I) Val (V); and
(e) Aromatic amino acids: Phe(F) Tyr(Y) Trp(W) His (H).

Substitutions of an amino acid in a peptide by another amino acid in the same group are referred to as a conservative substitution and may preserve the physicochemical characteristics of the original peptide. In contrast, substitutions of an amino acid in a peptide by another amino acid in a different group are generally more likely to alter the characteristics of the original peptide.

Examples of peptides that activate mu-opioid receptors include, but are not limited to, the aromatic-cationic peptides shown in Table 6.

TABLE 6

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Arg | Phe | Lys | NH$_2$ |
| Tyr | D-Arg | Phe | Orn | NH$_2$ |
| Tyr | D-Arg | Phe | Dab | NH$_2$ |
| Tyr | D-Arg | Phe | Dap | NH$_2$ |
| 2'6'Dmt | D-Arg | Phe | Lys | NH$_2$ |
| 2'6'Dmt | D-Arg | Phe | Lys-NH(CH$_2$)$_2$—NH-dns | NH$_2$ |
| 2'6'Dmt | D-Arg | Phe | Lys-NH(CH$_2$)$_2$—NH-atn | NH$_2$ |
| 2'6'Dmt | D-Arg | Phe | dnsLys | NH$_2$ |
| 2'6'Dmt | D-Cit | Phe | Lys | NH$_2$ |
| 2'6'Dmt | D-Cit | Phe | Ahp | NH$_2$ |
| 2'6'Dmt | D-Arg | Phe | Orn | NH$_2$ |
| 2'6'Dmt | D-Arg | Phe | Dab | NH$_2$ |
| 2'6'Dmt | D-Arg | Phe | Dap | NH$_2$ |
| 2'6'Dmt | D-Arg | Phe | Ahp(2-aminoheptanoic acid) | NH$_2$ |
| Bio-2'6'Dmt | D-Arg | Phe | Lys | NH$_2$ |
| 3'5'Dmt | D-Arg | Phe | Lys | NH$_2$ |
| 3'5'Dmt | D-Arg | Phe | Orn | NH$_2$ |
| 3'5'Dmt | D-Arg | Phe | Dab | NH$_2$ |
| 3'5'Dmt | D-Arg | Phe | Dap | NH$_2$ |

TABLE 6-continued

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Arg | Tyr | Lys | NH$_2$ |
| Tyr | D-Arg | Tyr | Orn | NH$_2$ |
| Tyr | D-Arg | Tyr | Dab | NH$_2$ |
| Tyr | D-Arg | Tyr | Dap | NH$_2$ |
| 2'6'Dmt | D-Arg | Tyr | Lys | NH$_2$ |
| 2'6'Dmt | D-Arg | Tyr | Orn | NH$_2$ |
| 2'6'Dmt | D-Arg | Tyr | Dab | NH$_2$ |
| 2'6'Dmt | D-Arg | Tyr | Dap | NH$_2$ |
| 2'6'Dmt | D-Arg | 2'6'Dmt | Lys | NH$_2$ |
| 2'6'Dmt | D-Arg | 2'6'Dmt | Orn | NH$_2$ |
| 2'6'Dmt | D-Arg | 2'6'Dmt | Dab | NH$_2$ |
| 2'6'Dmt | D-Arg | 2'6'Dmt | Dap | NH$_2$ |
| 3'5'Dmt | D-Arg | 3'5'Dmt | Arg | NH$_2$ |
| 3'5'Dmt | D-Arg | 3'5'Dmt | Lys | NH$_2$ |
| 3'5'Dmt | D-Arg | 3'5'Dmt | Orn | NH$_2$ |
| 3'5'Dmt | D-Arg | 3'5'Dmt | Dab | NH$_2$ |
| Tyr | D-Lys | Phe | Dap | NH$_2$ |
| Tyr | D-Lys | Phe | Arg | NH$_2$ |
| Tyr | D-Lys | Phe | Lys | NH$_2$ |
| Tyr | D-Lys | Phe | Orn | NH$_2$ |
| 2'6'Dmt | D-Lys | Phe | Dab | NH$_2$ |
| 2'6'Dmt | D-Lys | Phe | Dap | NH$_2$ |
| 2'6'Dmt | D-Lys | Phe | Arg | NH$_2$ |
| 2'6'Dmt | D-Lys | Phe | Lys | NH$_2$ |
| 3'5'Dmt | D-Lys | Phe | Orn | NH$_2$ |
| 3'5'Dmt | D-Lys | Phe | Dab | NH$_2$ |
| 3'5'Dmt | D-Lys | Phe | Dap | NH$_2$ |
| 3'5'Dmt | D-Lys | Phe | Arg | NH$_2$ |
| Tyr | D-Lys | Tyr | Lys | NH$_2$ |
| Tyr | D-Lys | Tyr | Orn | NH$_2$ |
| Tyr | D-Lys | Tyr | Dab | NH$_2$ |
| Tyr | D-Lys | Tyr | Dap | NH$_2$ |
| 2'6'Dmt | D-Lys | Tyr | Lys | NH$_2$ |
| 2'6'Dmt | D-Lys | Tyr | Orn | NH$_2$ |
| 2'6'Dmt | D-Lys | Tyr | Dab | NH$_2$ |
| 2'6'Dmt | D-Lys | Tyr | Dap | NH$_2$ |
| 2'6'Dmt | D-Lys | 2'6'Dmt | Lys | NH$_2$ |
| 2'6'Dmt | D-Lys | 2'6'Dmt | Orn | NH$_2$ |
| 2'6'Dmt | D-Lys | 2'6'Dmt | Dab | NH$_2$ |
| 2'6'Dmt | D-Lys | 2'6'Dmt | Dap | NH$_2$ |
| 2'6'Dmt | D-Arg | Phe | dnsDap | NH$_2$ |
| 2'6'Dmt | D-Arg | Phe | atnDap | NH$_2$ |
| 3'5'Dmt | D-Lys | 3'5'Dmt | Lys | NH$_2$ |
| 3'5'Dmt | D-Lys | 3'5'Dmt | Orn | NH$_2$ |
| 3'5'Dmt | D-Lys | 3'5'Dmt | Dab | NH$_2$ |
| 3'5'Dmt | D-Lys | 3'5'Dmt | Dap | NH$_2$ |
| Tyr | D-Lys | Phe | Arg | NH$_2$ |
| Tyr | D-Orn | Phe | Arg | NH$_2$ |
| Tyr | D-Dab | Phe | Arg | NH$_2$ |
| Tyr | D-Dap | Phe | Arg | NH$_2$ |
| 2'6'Dmt | D-Arg | Phe | Arg | NH$_2$ |
| 2'6'Dmt | D-Lys | Phe | Arg | NH$_2$ |
| 2'6'Dmt | D-Orn | Phe | Arg | NH$_2$ |
| 2'6'Dmt | D-Dab | Phe | Arg | NH$_2$ |
| 3'5'Dmt | D-Dap | Phe | Arg | NH$_2$ |
| 3'5'Dmt | D-Arg | Phe | Arg | NH$_2$ |
| 3'5'Dmt | D-Lys | Phe | Arg | NH$_2$ |
| 3'5'Dmt | D-Orn | Phe | Arg | NH$_2$ |
| Tyr | D-Lys | Tyr | Arg | NH$_2$ |
| Tyr | D-Orn | Tyr | Arg | NH$_2$ |
| Tyr | D-Dab | Tyr | Arg | NH$_2$ |
| Tyr | D-Dap | Tyr | Arg | NH$_2$ |
| 2'6'Dmt | D-Arg | 2'6'Dmt | Arg | NH$_2$ |
| 2'6'Dmt | D-Lys | 2'6'Dmt | Arg | NH$_2$ |
| 2'6'Dmt | D-Orn | 2'6'Dmt | Arg | NH$_2$ |
| 2'6'Dmt | D-Dab | 2'6'Dmt | Arg | NH$_2$ |
| 3'5'Dmt | D-Dap | 3'5'Dmt | Arg | NH$_2$ |
| 3'5'Dmt | D-Arg | 3'5'Dmt | Arg | NH$_2$ |
| 3'5'Dmt | D-Lys | 3'5'Dmt | Arg | NH$_2$ |
| 3'5'Dmt | D-Orn | 3'5'Dmt | Arg | NH$_2$ |
| Mmt | D-Arg | Phe | Lys | NH$_2$ |
| Mmt | D-Arg | Phe | Orn | NH$_2$ |
| Mmt | D-Arg | Phe | Dab | NH$_2$ |
| Mmt | D-Arg | Phe | Dap | NH$_2$ |
| Tmt | D-Arg | Phe | Lys | NH$_2$ |
| Tmt | D-Arg | Phe | Orn | NH$_2$ |
| Tmt | D-Arg | Phe | Dab | NH$_2$ |
| Tmt | D-Arg | Phe | Dap | NH$_2$ |
| Hmt | D-Arg | Phe | Lys | NH$_2$ |
| Hmt | D-Arg | Phe | Orn | NH$_2$ |
| Hmt | D-Arg | Phe | Dab | NH$_2$ |
| Hmt | D-Arg | Phe | Dap | NH$_2$ |
| Mmt | D-Lys | Phe | Lys | NH$_2$ |
| Mmt | D-Lys | Phe | Orn | NH$_2$ |
| Mmt | D-Lys | Phe | Dab | NH$_2$ |
| Mmt | D-Lys | Phe | Dap | NH$_2$ |
| Mmt | D-Lys | Phe | Arg | NH$_2$ |
| Tmt | D-Lys | Phe | Lys | NH$_2$ |
| Tmt | D-Lys | Phe | Orn | NH$_2$ |
| Tmt | D-Lys | Phe | Dab | NH$_2$ |
| Tmt | D-Lys | Phe | Dap | NH$_2$ |
| Tmt | D-Lys | Phe | Arg | NH$_2$ |
| Hmt | D-Lys | Phe | Lys | NH$_2$ |
| Hmt | D-Lys | Phe | Orn | NH$_2$ |
| Hmt | D-Lys | Phe | Dab | NH$_2$ |
| Hmt | D-Lys | Phe | Dap | NH$_2$ |
| Hmt | D-Lys | Phe | Arg | NH$_2$ |
| Mmt | D-Lys | Phe | Arg | NH$_2$ |
| Mmt | D-Orn | Phe | Arg | NH$_2$ |
| Mmt | D-Dab | Phe | Arg | NH$_2$ |
| Mmt | D-Dap | Phe | Arg | NH$_2$ |
| Mmt | D-Arg | Phe | Arg | NH$_2$ |
| Tmt | D-Lys | Phe | Arg | NH$_2$ |
| Tmt | D-Orn | Phe | Arg | NH$_2$ |
| Tmt | D-Dab | Phe | Arg | NH$_2$ |
| Tmt | D-Dap | Phe | Arg | NH$_2$ |
| Tmt | D-Arg | Phe | Arg | NH$_2$ |
| Hmt | D-Lys | Phe | Arg | NH$_2$ |
| Hmt | D-Orn | Phe | Arg | NH$_2$ |
| Hmt | D-Dab | Phe | Arg | NH$_2$ |
| Hmt | D-Dap | Phe | Arg | NH$_2$ |
| Hmt | D-Arg | Phe | Arg | NH$_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α, β -diaminopropionic acid
atnDap = β-anthraniloyl-L-α, β-diaminopropionic acid
Bio = biotin Examples of peptides that do not activate mu-opioid receptors include, but are not limited to, the aromatic-cationic peptides shown in Table 7.

TABLE 7

Peptide Analogs Lacking Mu-Opioid Activity

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | NH$_2$ |
| D-Arg | Dmt | Phe | Lys | NH$_2$ |
| D-Arg | Phe | Lys | Dmt | NH$_2$ |
| D-Arg | Phe | Dmt | Lys | NH$_2$ |
| D-Arg | Lys | Dmt | Phe | NH$_2$ |
| D-Arg | Lys | Phe | Dmt | NH$_2$ |
| Phe | Lys | Dmt | D-Arg | NH$_2$ |
| Phe | Lys | D-Arg | Dmt | NH$_2$ |
| Phe | D-Arg | Phe | Lys | NH$_2$ |
| Phe | D-Arg | Dmt | Lys | NH$_2$ |
| Phe | D-Arg | Lys | Dmt | NH$_2$ |
| Phe | Dmt | D-Arg | Lys | NH$_2$ |

TABLE 7-continued

Peptide Analogs Lacking Mu-Opioid Activity

| Amino Acid Position 1 | Amino Acid Position 2 | Amino Acid Position 3 | Amino Acid Position 4 | C-Terminal Modification |
|---|---|---|---|---|
| Phe | Dmt | Lys | D-Arg | $NH_2$ |
| Lys | Phe | D-Arg | Dmt | $NH_2$ |
| Lys | Phe | Dmt | D-Arg | $NH_2$ |
| Lys | Dmt | D-Arg | Phe | $NH_2$ |
| Lys | Dmt | Phe | D-Arg | $NH_2$ |
| Lys | D-Arg | Phe | Dmt | $NH_2$ |
| Lys | D-Arg | Dmt | Phe | $NH_2$ |
| D-Arg | Dmt | D-Arg | Phe | $NH_2$ |
| D-Arg | Dmt | D-Arg | Dmt | $NH_2$ |
| D-Arg | Dmt | D-Arg | Tyr | $NH_2$ |
| D-Arg | Dmt | D-Arg | Trp | $NH_2$ |
| Trp | D-Arg | Phe | Lys | $NH_2$ |
| Trp | D-Arg | Tyr | Lys | $NH_2$ |
| Trp | D-Arg | Trp | Lys | $NH_2$ |
| Trp | D-Arg | Dmt | Lys | $NH_2$ |
| D-Arg | Trp | Lys | Phe | $NH_2$ |
| D-Arg | Trp | Phe | Lys | $NH_2$ |
| D-Arg | Trp | Lys | Dmt | $NH_2$ |
| D-Arg | Trp | Dmt | Lys | $NH_2$ |
| D-Arg | Lys | Trp | Phe | $NH_2$ |
| D-Arg | Lys | Trp | Dmt | $NH_2$ |
| Cha | D-Arg | Phe | Lys | $NH_2$ |
| Ala | D-Arg | Phe | Lys | $NH_2$ |

Cha = cyclohexyl alanine

The amino acids of the peptides shown in Table 6 and 7 may be in either the L- or the D-configuration.

The peptides may be synthesized by any of the methods well known in the art. Suitable methods for chemically synthesizing the protein include, for example, those described by Stuart and Young in Solid Phase Peptide Synthesis, Second Edition, Pierce Chemical Company (1984), and in Methods Enzymol., 289, Academic Press, Inc., New York (1997).

Synthesis of the Aromatic-Cationic Peptides of the Present Technology

The aromatic-cationic peptides useful in the methods of the present technology may be chemically synthesized by any of the methods well known in the art. Suitable methods for synthesizing the protein include, for example, those described by Stuart and Young in "Solid Phase Peptide Synthesis," Second Edition, Pierce Chemical Company (1984), and in "Solid Phase Peptide Synthesis," Methods Enzymol. 289, Academic Press, Inc, New York (1997).

In practicing the present technology, many conventional techniques in molecular biology, protein biochemistry, cell biology, immunology, microbiology and recombinant DNA are used. These techniques are well-known and are explained in, e.g., Current Protocols in Molecular Biology, Vols. I-III, Ausubel, Ed. (1997); Sambrook et al., Molecular Cloning: A Laboratory Manual, Second Ed. (Cold Spring Harbor Laboratory Press, Cold Spring Harbor, N.Y., 1989); DNA Cloning: A Practical Approach, Vols. I and II, Glover, Ed. (1985); Oligonucleotide Synthesis, Gait, Ed. (1984); Nucleic Acid Hybridization, Hames & Higgins, Eds. (1985); Transcription and Translation, Hames & Higgins, Eds. (1984); Animal Cell Culture, Freshney, Ed. (1986); Immobilized Cells and Enzymes (IRL Press, 1986); Perbal, A Practical Guide to Molecular Cloning; the series, Meth. Enzymol., (Academic Press, Inc., 1984); Gene Transfer Vectors for Mammalian Cells, Miller & Calos, Eds. (Cold Spring Harbor Laboratory, NY, 1987); and Meth. Enzymol., Vols. 154 and 155, Wu & Grossman, and Wu, Eds., respectively.

III Use of Monocytes in Diagnostic Methods

The cellular components of peripheral blood include red blood cells, white blood cells, and platelets. White blood cells, or leukocytes, are cells of the immune system involved in defending the body against both infectious disease and foreign materials. Five different and diverse types of leukocytes exist: neutrophils, basophils, and eosinophils (together the granulocytes or polymorphonuclear leukocytes), lymphocytes and monocytes (together the agranulocytes, mononuclear leukocytes or peripheral blood mononuclear cells (PBMCs)). The three major types of lymphocyte (all from the lymphoid lineage) are T cells and B cells (the major cellular components of the adaptive immune response) and natural killer (NK) cells. Monocytes are derived from the myeloid lineage and are part of the innate immune system and are able to migrate quickly to a site of inflammation in the body. Circulating monocytes present in whole blood can give rise to macrophages and dendritic cells.

Currently, the most common approaches to measure cellular bioenergetics have been to isolate mitochondria from biopsies, peripheral blood cells or develop fibroblast cell lines from patient samples. The drawback of these approaches is that PBMC do not have high levels of mitochondria, biopsies are generally invasive and painful, and in the case of fibroblasts the passage of the cells may alter their bioenergetics.

Levels and/or biomarkers of mitochondrial physiology of circulating monocytes are altered from the very earliest stages of a disease or condition. Many such diseases or conditions are associated with mitochondrial dysfunction. In some embodiments, the disease or condition is an inflammatory disease or a disease with an inflammatory component such as ischemia, stroke, renal injury, neurodegenerative diseases, atherosclerosis, metabolic syndrome, acute myocardial infarction, heart failure, ischemia reperfusion, ureteral obstruction, diabetic nephropathy, diabetes, Leber's Heredity Optic Neuropathy (LHON), Dominant Optic Atrophy (DOA), Barth's syndrome, POLG disease, and Leigh's disease. In some embodiments, the neurodegenerative disease is Alzheimer's disease, Amyotrophic Lateral Sclerosis (ALS), Huntington's disease, Friedreich's ataxia, or Multiple Sclerosis. In principle, for each of these inflammatory diseases a specific monocyte signature can be derived, comprising at least one physiological parameter that is differentially regulated in monocytes. These observed physiological differences of circulating monocytes are caused by factors associated with the disease or condition characterized by mitochondrial dysfunction, such as increased oxidative stress or defects in mitochondrial permeability transition. The differences in the levels and/or biomarkers of mitochondrial physiology of circulating monocytes can be used as accurate and sensitive methods for detecting and diagnosing diseases or conditions characterized by mitochondrial dysfunction in a subject. The biomarkers of mitochondrial physiology described herein can be evaluated in a minimally invasive way, as only a small sample of (typically peripheral) blood is required. Moreover, a subset of parameters in the monocyte physiological profile can be used to discriminate between patients with different types and/or severities of diseases or conditions characterized by mitochondrial dysfunction. This allows stratification of patients, and may help guide decisions on suitable therapies.

In one aspect, the present technology provides a method for identifying a disease or condition characterized by mitochondrial dysfunction in a subject, comprising (a) assaying the level of a population of activated monocytes present in a biological sample obtained from the subject, and (b) comparing the level of the population of activated monocytes observed in step (a) with the level of a corresponding population of activated monocytes observed in a reference sample, wherein the subject is identified as having a disease or condition characterized by mitochondrial dysfunction if the level of the population of activated monocytes present in the biological sample is increased compared to the reference sample.

In some embodiments, the reference sample is a biological sample obtained from a healthy subject.

In some embodiments, the total count of activated monocytes present in the biological sample is increased compared to the reference sample. In some embodiments, the level of classical monocytes ($CD14^{high}$ $CD16^-$) is elevated compared to the reference sample. In some embodiments, the level of intermediate monocytes ($CD14^{high}CD16^+$) is elevated compared to the reference sample. In a further embodiment, the level of non-classical monocytes ($CD14^{low}CD16^{high}$) is decreased compared to the reference sample. In some embodiments, the monocytes are circulating monocytes. In other embodiments, the monocytes are extravasated from the bloodstream to other tissues.

Suitable techniques to determine overall monocyte count as well as the distribution of the different types of monocytes include flow cytometry or FACS. In particular, FACS analysis can be used to determine if there is an expansion or alteration of a given subpopulation of monocytes, thereby unmasking a signal that may otherwise be undetectable in a whole blood sample. Such alterations serve as a predictor of a disease state or condition characterized by mitochondrial dysfunction. Many of these techniques can also be done using alternatives to classical antibodies, e.g. nanobodies (single domain antibodies, developed by Ablynx), alphabodies (single-chain, triple-stranded coiled coil proteins, developed by Complix) or other protein-binding molecules.

In some embodiments, the disease or condition characterized by mitochondrial dysfunction is ischemia, stroke, renal injury, neurodegenerative disease, atherosclerosis, metabolic syndrome, acute myocardial infarction, heart failure, ischemia reperfusion, ureteral obstruction, diabetic nephropathy, diabetes, Leber's Heredity Optic Neuropathy (LHON), Dominant Optic Atrophy (DOA), Barth's syndrome, POLG disease, or Leigh's disease. In some embodiments, the neurodegenerative disease is Alzheimer's disease, Amyotrophic Lateral Sclerosis (ALS), Huntington's disease, Friedreich's ataxia or Multiple Sclerosis.

In some embodiments, the biological sample is a blood sample. In certain embodiments, the monocytes are isolated from a blood sample (e.g., peripheral or central blood sample). In a particular embodiment, the blood sample is obtained no more than 12 hours, no more than 10 hours, no more than 8 hours, no more than 6 hours, no more than 4 hours or no more than 2 hours prior to starting the isolation of the monocytes from the blood sample.

In another embodiment, the present technology provides a method for identifying a disease or condition characterized by mitochondrial dysfunction in a subject, comprising (a) assaying the ratio of different monocyte types present in a biological sample obtained from the subject, and (b) comparing the ratio of different monocyte types observed in step (a) with the ratio of corresponding monocyte types observed in a reference sample, wherein the subject is identified as having a disease or condition characterized by mitochondrial dysfunction if the ratio of different monocyte types present in the biological sample is altered compared to the reference sample.

In some embodiments, the reference sample is a biological sample obtained from a healthy subject. In some embodiments, the monocytes are circulating monocytes. In other embodiments, the monocytes are extravasated from the bloodstream to other tissues. In some embodiments, the ratio of activated monocytes to non-classical monocytes is elevated compared to the reference sample. In some embodiments, the ratio of classical monocytes to non-classical monocytes is elevated compared to the reference sample. In some embodiments, the ratio of intermediate monocytes to non-classical monocytes is elevated compared to the reference sample. In certain embodiments, the ratio of classical monocytes to intermediate monocytes is elevated compared to the reference sample.

In some embodiments, the disease or condition characterized by mitochondrial dysfunction is ischemia, stroke, renal injury, neurodegenerative disease, atherosclerosis, metabolic syndrome, acute myocardial infarction, heart failure, ischemia reperfusion, ureteral obstruction, diabetic nephropathy, diabetes, Leber's Heredity Optic Neuropathy (LHON), Dominant Optic Atrophy (DOA), Barth's syndrome, POLG disease, or Leigh's disease. In some embodiments, the neurodegenerative disease is Alzheimer's disease, Amyotrophic Lateral Sclerosis (ALS), Huntington's disease, Friedreich's ataxia or Multiple Sclerosis.

In another embodiment, the present technology provides a method for identifying a disease or condition characterized by mitochondrial dysfunction in a subject, comprising (a) assaying at least one biomarker of mitochondrial physiology of a population of monocytes present in a biological sample obtained from the subject, and (b) comparing the biomarker of mitochondrial physiology of the population of monocytes observed in step (a) with the biomarker of mitochondrial physiology of a corresponding population of monocytes observed in a reference sample, wherein the subject is identified as having a disease or condition characterized by mitochondrial dysfunction if the biomarker of mitochondrial physiology of the population of monocytes present in the biological sample is altered compared to the reference sample.

In some embodiments, the reference sample is a biological sample obtained from a healthy subject. In some embodiments, the monocytes are circulating monocytes. In other embodiments, the monocytes are extravasated from the bloodstream to other tissues.

In some embodiments, the disease or condition characterized by mitochondrial dysfunction is ischemia, stroke, renal injury, neurodegenerative disease, atherosclerosis, metabolic syndrome, acute myocardial infarction, heart failure, ischemia reperfusion, ureteral obstruction, diabetic nephropathy, diabetes, Leber's Heredity Optic Neuropathy (LHON), Dominant Optic Atrophy (DOA), Barth's syndrome, POLG disease, or Leigh's disease. In some embodiments, the neurodegenerative disease is Alzheimer's disease, Amyotrophic Lateral Sclerosis (ALS), Huntington's disease, Friedreich's ataxia or Multiple Sclerosis.

In some embodiments, the disease or condition characterized by mitochondrial dysfunction results in a disruption in oxidative phosphorylation. A sample of monocytes can be evaluated for disruption in oxidative phosphorylation using assays well known in the art. Typically, the methods will be performed in vitro. By way of example, but not by way of limitation, a disruption in oxidative phosphorylation is determined by assays that measures levels of coenzyme $Q_{10}$ (CoQ10). In some embodiments, disruption in oxidative phosphorylation is determined by assays that measure OXPHOS capacity by the uncoupling ratio. In some embodiments, disruption in oxidative phosphorylation is determined by assays that measure the net routine flux control ratio. In some embodiments, disruption in oxidative phosphorylation is determined by assays that measure leak flux control ratio. In some embodiments, disruption in oxidative phosphorylation is determined by assays that measure the phosphorylation respiratory control ratio.

Uncoupling ratio (UCR) is an expression of the respiratory reserve capacity and indicates the OXPHOS capacity of the cells. In some embodiments, UCR is defined as $Cr_u/Cr$. $Cr_u$ is the maximum rate of oxygen utilization (Oxygen flux) produced when mitochondria are chemically uncoupled using FCCP (Carbonyl cyanide 4-(trifluoromethoxy) phenylhydrazone). FCCP titration must be performed since the concentration of FCCP required to produce maximum oxygen utilization varies among different cell lines. Once the maximum oxygen utilization is reached, further increases in FCCP inhibit oxygen utilization by oxidative phosphorylation. In some embodiments, Cr represents oxygen utilization by the cells during a normal cellular respiration with excess substrates.

In some embodiments, the Net Routine Flux Control Ratio ($Cr/Cr_u$) is the inverse of the UCR. In some embodiments, this value assesses how close routine respiration operates to the respiratory capacity of oxidative phosphorylation.

In some embodiments, the Respiratory Control Ratio (RCR) is defined as $Cr_u/Cr_o$. $Cr_u$ is defined above. $Cr_o$=Respiration after inhibition of Complex V (ATP synthase) by oligomycin. In some embodiments, this ratio allows assessment of uncoupling and OXPHOS dysfunction.

In some embodiments, the Leak Flux Control Ratio is determined by $Cr_o/Cr_u$. In some embodiments, this parameter is the inverse of RCR and represents proton leak with inhibition of ADP phosphorylation by oligomycin.

In some embodiments, the Phosphorylation Respiratory Control Ratio (RCRp) is defined as $(Cr-Cr_o)/Cr_u$ (or 1/UCR−1/RCR). In some embodiments, the RCRp is an index which expresses phosphorylation-related respiration $(Cr-Cr_o)$ as a function of respiratory capacity $(Cr_u)$. In some embodiments, the RCRp remains constant, if partial uncoupling is fully compensated by an increased routine respiration rate and a constant rate of oxidative phosphorylation is maintained. In some embodiments, if the respiratory capacity declines without effect on the rate of oxidative phosphorylation; in some embodiments, the RCRp increases, which indicates that a higher proportion of the maximum capacity is activated to drive ATP synthesis. In some embodiments, the RCRp declines to zero in either fully uncoupled cells or in cells under complete metabolic arrest.

In another embodiment, the methods of the present technology can be used to monitor biomarkers of mitochondrial physiology in a sample of monocytes to assess the presence or absence of a disease or condition characterized by mitochondrial dysfunction in a subject.

In some embodiments, alterations in the biomarkers of mitochondrial physiology of monocytes can be detected by assaying the levels of one or more biomarkers of mitochondrial physiology selected from the group consisting of lactic acid (lactate) levels, pyruvic acid (pyruvate) levels, lactate/pyruvate ratios, phosphocreatine levels, NADH (NADH+ $H^{30}$) or NADPH (NADPH+$H^{30}$) levels; NAD or NADP levels; ATP levels; reduced coenzyme Q (CoQred) levels; oxidized coenzyme Q (CoQox) levels; total coenzyme Q (CoQtot) levels; oxidized cytochrome C levels; reduced cytochrome C levels; oxidized cytochrome C/reduced cytochrome C ratio; acetoacetate levels; beta-hydroxy butyrate levels; acetoacetate/beta-hydroxy butyrate ratio; 8-hydroxy-2'-deoxyguanosine (8-OHdG) levels; levels of reactive oxygen species; oxygen consumption (VO2), carbon dioxide output (VCO2), and respiratory quotient (VCO2/VO2). In some embodiments, lactic acid (lactate) levels can be determined by assaying lactic acid (lactate) levels in whole blood, plasma, cerebrospinal fluid, or cerebral ventricular fluid. In some embodiments, pyruvic acid (pyruvate) levels can be determined by assaying pyruvic acid (pyruvate) levels in whole blood, plasma, cerebrospinal fluid, or cerebral ventricular fluid. In some embodiments, lactate/pyruvate ratios can be determined by assaying lactate/pyruvate ratios in whole blood, plasma, cerebrospinal fluid, or cerebral ventricular fluid.

Several of these biomarkers of mitochondrial physiology are discussed in more detail as follows. It should be emphasized that, while certain biomarkers of mitochondrial physiology are discussed and enumerated herein, the present technology is not limited to modulation, normalization or enhancement of only these enumerated biomarkers of mitochondrial physiology in a sample of monocytes.

Pyruvate, a product of the anaerobic metabolism of glucose, is removed by reduction to lactic acid in an anaerobic setting or by oxidative metabolism, which is dependent on a functional mitochondrial respiratory chain. Dysfunction of the respiratory chain may lead to inadequate removal of lactate and pyruvate from the circulation and elevated lactate/pyruvate ratios are observed in mitochondrial cytopathies (see Scriver C R, *The Metabolic and Molecular Bases of Inherited Disease,* 7th ed., New York: McGraw-Hill, Health Professions Division, 1995; and Munnich et al., *J. Inherit. Metab. Dis.* 15(4):448-55 (1992)). Blood lactate/pyruvate ratio (Chariot et al., *Arch. Pathol. Lab. Med.* 118(7):695-7 (1994)) is, therefore, widely used as a noninvasive test for detection of mitochondrial cytopathies (see again Scriver C R, *The Metabolic and Molecular Bases of Inherited Disease,* 7th ed., New York: McGraw-Hill, Health Professions Division, 1995; and Munnich et al., *J. Inherit. Metab. Dis.* 15(4):448-55 (1992)) and toxic mitochondrial myopathies (Chariot et al., *Arthritis Rheum.* 37(4):583-6 (1994)). Changes in the redox state of mitochondria can be investigated by measuring the arterial ketone body ratio (acctoacetate/3-hydroxybutyrate: AKBR) (Ueda et al., *J. Cardiol.* 29(2):95-102 (1997)). Urinary excretion of 8-hydroxy-2'-deoxyguanosine (8-OHdG) often has been used as a biomarker to assess the extent of repair of ROS-induced DNA damage in both clinical and occupational settings (Erhola et al., *FEBS Lett.* 409(2):287-91 (1997); Honda et al., *Leuk. Res.* 24(6):461-8 (2000); Pilger et al., *Free Radic. Res.* 35(3):273-80 (2001); Kim et al. *Environ Health Perspect* 112(6):666-71 (2004)).

Lactic acid (lactate) levels: Mitochondrial dysfunction typically results in abnormal levels of lactic acid, as pyruvate levels increase and pyruvate is converted to lactate to maintain capacity for glycolysis. Mitochondrial dysfunction can also result in abnormal levels of NADH+$H^{30}$, NADPH+$H^{30}$, NAD, or NADP, as the reduced nicotinamide adenine dinucleotides are not efficiently processed by the respiratory chain. Lactate levels can be measured by taking samples of appropriate bodily fluids such as whole blood, plasma, or cerebrospinal fluid. Using magnetic resonance, lactate levels can be measured in virtually any volume of the body desired, such as the brain. Measurement of cerebral lactic acidosis using magnetic resonance in patients is described in Kaufmann et al., *Neurology* 62(8): 1297 (2004). Whole blood, plasma, and cerebrospinal fluid lactate levels can be measured by commercially available equipment such as the YSI 2300 STAT Plus Glucose & Lactate Analyzer (YSI Life Sciences, Ohio).

NAD, NADP, NADH and NADPH levels: Measurement of NAD, NADP, NADH) (NADH+H$^{30}$) or NADPH (NADPH+H$^{30}$) can be measured by a variety of fluorescent, enzymatic, or electrochemical techniques, e.g., the electrochemical assay described in US 2005/0067303.

Oxygen consumption ($vO_2$ or VO2), carbon dioxide output ($vCO_2$ or VCO2), and respiratory quotient (VCO2/VO2): $vO_2$ is usually measured either while resting (resting $vO_2$) or at maximal exercise intensity ($vO_2$ max). Optimally, both values will be measured. Measurement of both forms of $vO_2$ is readily accomplished using standard equipment from a variety of vendors, e.g., Korr Medical Technologies, Inc. (Salt Lake City, Utah). VCO2 can also be readily measured, and the ratio of VCO2 to VO2 under the same conditions (VCO2/VO2, either resting or at maximal exercise intensity) provides the respiratory quotient (RQ).

Oxidized Cytochrome C, reduced Cytochrome C, and ratio of oxidized Cytochrome C to reduced Cytochrome C: Cytochrome C parameters, such as oxidized cytochrome C levels (Cyt $C_{ox}$), reduced cytochrome C levels (Cyt $C_{red}$), and the ratio of oxidized cytochrome C/reduced cytochrome C ratio (Cyt $C_{ox}$)/(Cyt $C_{red}$), can be measured by in vivo near infrared spectroscopy. See, e.g., Rolfe, P., "In vivo near-infrared spectroscopy," *Annu. Rev. Biomed. Eng.* 2:715-54 (2000) and Strangman et al., "Non-invasive neuroimaging using near-infrared light" *Biol. Psychiatry* 52:679-93 (2002).

Similarly, tests for normal and abnormal values of pyruvic acid (pyruvate) levels, lactate/pyruvate ratio, ATP levels, anaerobic threshold, reduced coenzyme Q ($CoQ^{red}$) levels, oxidized coenzyme Q ($CoQ^{ox}$) levels, total coenzyme Q ($CoQ^{tot}$) levels, oxidized cytochrome C levels, reduced cytochrome C levels, oxidized cytochrome C/reduced cytochrome C ratio, acetoacetate levels, β-hydroxy butyrate levels, acetoacetate/β-hydroxy butyrate ratio, 8-hydroxy-2'-deoxyguanosine (8-OHdG) levels, and levels of reactive oxygen species are known in the art and can be used to derive a metabolic signature for a biological sample (e.g., monocytes). For the purposes of the present technology, modulation, normalization, or enhancement of biomarker of mitochondrial physiology includes modulation, normalization, or enhancement of anaerobic threshold in monocytes.

In some embodiments, alterations in the biomarkers of mitochondrial physiology of monocytes can be evaluated using magnetic resonance spectroscopy (MRS). MRS has been useful in the diagnoses of mitochondrial cytopathy by demonstrating elevations in cerebrospinal fluid (CSF) and cortical white matter lactate using proton MRS (1H-MRS) (Kaufmann et al., *Neurology* 62(8):1297-302 (2004)). Phosphorous MRS (31P-MRS) has been used to demonstrate low levels of cortical phosphocreatine (PCr) (Matthews et al., *Ann. Neurol.* 29(4):435-8 (1991)), and a delay in PCr recovery kinetics following exercise in skeletal muscle (Matthews et al., *Ann. Neurol.* 29(4):435-8 (1991); Barbiroli et al., *J. Neurol.* 242(7):472-7 (1995); Fabrizi et al., *J. Neural. Sci.* 137(1):20-7 (1996)). A low skeletal muscle PCr has also been confirmed in patients with mitochondrial cytopathy by direct biochemical measurements.

Additionally, high-resolution respirometry (HRR) of monocytes offer sensitive diagnostic tests of integrated mitochondrial function using standard cell culture techniques and small needle tissue biopsies. Multiple substrate-uncoupler-inhibitor titration (SUIT) protocols for analysis of oxidative phosphorylation can aid in the dissection of mitochondrial respiratory control and the pathophysiology of mitochondrial diseases. Respiratory states are defined in functional terms to account for the network of metabolic interactions in complex SUIT protocols with stepwise modulation of coupling and substrate control. A regulated degree of intrinsic uncoupling is a hallmark of oxidative phosphorylation, whereas pathological and toxicological dyscoupling is evaluated as a mitochondrial defect. The non-coupled state of maximum respiration is experimentally induced by titration of established uncouplers (FCCP, DNP), to collapse the proton gradient across the mitochondrial inner membrane and measure the capacity of the electron transfer system (ETS, open-circuit operation of respiration). Intrinsic uncoupling and dyscoupling are evaluated as the flux control ratio between non-phosphorylating LEAK respiration (electron flow coupled to proton pumping to compensate for proton leaks) and ETS capacity. If OXPHOS capacity (maximally ADP stimulated oxygen flux) is less than ETS capacity, the phosphorylation system contributes to flux control. Physiological Complex I+II substrate combinations support maximum ETS and OXPHOS capacities, due to the additive effect of multiple electron supply pathways converging at the Q-junction. Substrate control with electron entry separately through Complex I (pyruvate+malate or glutamate+malate) or Complex II (succinate+rotenone) restricts ETS capacity and artificially enhances flux control upstream of the Q-cycle, providing diagnostic information on specific branches of the ETS. In some embodiments, HRR measurements are accompanied by the fluorometric detection of reactive oxygen species (ROS; oxidative stress), ATP and $Ca^{2+}$ production, pH and mitochondrial membrane potential using established fluorescent dyes. A detailed description of HRR is provided in Gnaiger E (2012), *Mitochondr Physiol Network* 17.18. OROBOROS MiPNet Publications, Innsbruck: 64 pp, herein incorporated by reference in its entirety.

In some embodiments, the mitochondrial function of monocytes is assessed by simultaneously measuring the basal oxygen consumption, glycolysis rates, ATP production, and respiratory capacity of a sample of monocytes in a single experimental set up. By way of example, XF Analyzers (Seahorse Biosciences) perform cellular bioenergetics assays by combining an electro-optical instrument with 'smart plastic' cartridges that enable the real-time measurement of cellular bioenergetics in a non-invasive, high throughput multi-well (e.g., 96-well) microplate format. By incorporating automated compound addition and solid-state fluorescence sensors in a microplate format, such platforms determine in vitro oxygen consumption rate (OCR), and extracellular acidification rate (ECAR), so as to assess cellular functions such as oxidative phosphorylation, glycolysis, and fatty acid oxidation. High throughput bioenergetics platforms can be used to study respiratory malfunction in multiple disease states such as ischemia, stroke, renal injury, atherosclerosis, metabolic syndrome, acute myocardial infarction, heart failure, ischemia reperfusion, ureteral obstruction, diabetic nephropathy, diabetes, Leber's Heredity Optic Neuropathy (LHON), Dominant Optic Atrophy (DOA), Barth's syndrome, POLG disease, Leigh's disease, and neurodegenerative diseases such as Alzheimer's disease, Amyotrophic Lateral Sclerosis (ALS), Friedreich's ataxia, Huntington's disease or Multiple Sclerosis. Respiratory abnormalities in monocytes may arise as a result of environmental insult, mitochondrial DNA or nuclear DNA mutation.

In some embodiments, the high throughput bioenergetics platforms facilitate rapid detection of monocyte responses to substrates, inhibitors, and other perturbants. In another embodiment, monocytes are assayed via high throughput bioenergetics platforms in order to identify subjects that have or are suspected of having a disease or condition characterized by mitochondrial dysfunction. In some embodiments, these high throughput bioenergetics platforms permit the testing of multiple conditions per assay well.

Alterations in the levels and/or biomarkers of mitochondrial physiology of monocytes (compared to that observed in a healthy subject) can occur as a result of transient events such as tissue degeneration, stroke, or cardiovascular disease. In certain embodiments, the altered physiological profile of isolated monocytes permits the identification of such transient events. In other embodiments, the altered physiological profile of isolated monocytes provides an estimate of the frequency at which such transient events occur. In some embodiments, the altered physiological profile of isolated monocytes provides information on the timing of such transient events. The methods disclosed herein can thus be used to classify the extent/severity of the damage to the subject, which is subsequently useful in identifying the proper course of treatment.

IV Use of Monocytes to Evaluate the Therapeutic Effect of Aromatic-Cationic Peptides of the Present Technology In various embodiments, suitable in vitro or in vivo assays are performed to determine the biological effect of a specific aromatic-cationic peptide of the present technology and whether its administration is indicated for treatment. In various embodiments, in vitro assays can be performed with representative animal models, to determine if a given therapeutic (e.g., an aromatic-cationic peptide) exerts the desired effect in reducing disruption of mitochondrial function, such as disruption of OXPHOS. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

One aspect of the present technology provides a method for evaluating the therapeutic efficacy of an aromatic-cationic peptide on a disease or condition characterized by mitochondrial dysfunction in a subject, comprising (a) assaying the level of a population of activated monocytes present in a biological sample obtained from the subject, and (b) comparing the level of the population of activated monocytes observed in step (a) with the level of a corresponding population of activated monocytes observed in a biological sample obtained from the subject following administration of a dose of an aromatic-cationic peptide, wherein the aromatic-cationic peptide is identified as having a therapeutic effect on the disease or condition characterized by mitochondrial dysfunction if the level of the population of activated monocytes in the biological sample following the administration of the aromatic-cationic peptide is reduced compared to the level of the population of activated monocytes observed in step (a).

In some embodiments, the aromatic-cationic peptide is Phe-D-Arg-Phe-Lys-NH$_2$ or D-Arg-2'6'Dmt-Lys-Phe-NH$_2$ or a pharmaceutically acceptable salt thereof.

In some embodiments, the level of classical monocytes (CD14$^{high}$ CD16$^-$) in the biological sample following the administration of the aromatic-cationic peptide is reduced compared to the level of classical monocytes observed in step (a). In some embodiments, the level of intermediate monocytes (CD14$^{high}$CD16$^+$) in the biological sample following the administration of the aromatic-cationic peptide is reduced compared to the level of intermediate monocytes observed in step (a). In a further embodiment, the level of non-classical monocytes (CD14$^{low}$CD16$^{high}$) in the biological sample following the administration of the aromatic-cationic peptide is increased compared to the level of non-classical monocytes observed in step (a).

In some embodiments, the monocytes are circulating monocytes. In other embodiments, the monocytes are extravasated from the bloodstream to other tissues.

In some embodiments, the disease or condition characterized by mitochondrial dysfunction is ischemia, stroke, renal injury, neurodegenerative disease, atherosclerosis, metabolic syndrome, acute myocardial infarction, heart failure, ischemia reperfusion, ureteral obstruction, diabetic nephropathy, diabetes, Leber's Heredity Optic Neuropathy (LHON), Dominant Optic Atrophy (DOA), Barth's syndrome, POLG disease, or Leigh's disease. In some embodiments, the neurodegenerative disease is Alzheimer's disease, Amyotrophic Lateral Sclerosis (ALS), Huntington's disease, Friedreich's ataxia or Multiple Sclerosis.

In another embodiment, the present technology provides a method for evaluating the therapeutic efficacy of an aromatic-cationic peptide on a disease or condition characterized by mitochondrial dysfunction in a subject, comprising (a) assaying the ratio of different monocyte types present in a biological sample obtained from the subject, and (b) comparing the ratio of different monocyte types observed in step (a) with the ratio of corresponding monocyte types observed in a biological sample obtained from the subject following administration of a dose of an aromatic-cationic peptide, wherein the aromatic-cationic peptide is identified as having a therapeutic effect on the disease or condition characterized by mitochondrial dysfunction if the ratio of different monocyte types in the biological sample following the administration of the aromatic-cationic peptide is altered compared to the ratio of different monocyte types observed in step (a).

In some embodiments, the monocytes are circulating monocytes. In other embodiments, the monocytes are extravasated from the bloodstream to other tissues.

In some embodiments, the ratio of activated monocytes to non-classical monocytes in the biological sample following the administration of the aromatic-cationic peptide is reduced compared to the ratio of activated monocytes to non-classical monocytes observed in step (a). In some embodiments, the ratio of classical monocytes to non-classical monocytes in the biological sample following the administration of the aromatic-cationic peptide is reduced compared to the ratio of classical monocytes to non-classical monocytes observed in step (a). In some embodiments, the ratio of intermediate monocytes to non-classical monocytes in the biological sample following the administration of the aromatic-cationic peptide is reduced compared to the ratio of intermediate monocytes to non-classical monocytes observed in step (a).

In some embodiments, the ratio of classical monocytes to intermediate monocytes in the biological sample following the administration of the aromatic-cationic peptide is reduced compared to the ratio of classical monocytes to intermediate monocytes observed in step (a).

In some embodiments, the disease or condition characterized by mitochondrial dysfunction is ischemia, stroke, renal injury, neurodegenerative disease, atherosclerosis, metabolic syndrome, acute myocardial infarction, heart failure, ischemia reperfusion, ureteral obstruction, diabetic nephropathy, diabetes, Leber's Heredity Optic Neuropathy (LHON), Dominant Optic Atrophy (DOA), Barth's syndrome, POLG disease, or Leigh's disease. In some embodiments, the neurodegenerative disease is Alzheimer's disease, Amyotrophic Lateral Sclerosis (ALS), Huntington's disease, Friedreich's ataxia or Multiple Sclerosis.

In another embodiment, the present technology provides a method for evaluating the therapeutic efficacy of an aromatic-cationic peptide on a disease or condition characterized by mitochondrial dysfunction in a subject, comprising (a) assaying at least one biomarker of mitochondrial physiology of a population of monocytes present in a biological sample obtained from the subject, and (b) comparing the biomarker of mitochondrial physiology of the population of monocytes observed in step (a) with the biomarker of mitochondrial physiology of a corresponding population of monocytes observed in a biological sample obtained from the subject following administration of a dose of an aromatic-cationic peptide, wherein the aromatic-cationic peptide is identified as having a therapeutic effect on the disease or condition characterized by mitochondrial dysfunction if the biomarker of mitochondrial physiology of the population of monocytes in the biological sample following the administration of the aromatic-cationic peptide is similar to the biomarker of mitochondrial physiology of a corresponding population of monocytes in a reference sample. In some embodiments, the reference sample is a biological sample obtained from a healthy subject.

In some embodiments, the aromatic-cationic peptide is Phe-D-Arg-Phe-Lys-NH$_2$ or D-Arg-2'6'Dmt-Lys-Phe-NH$_2$ or a pharmaceutically acceptable salt thereof. In some embodiments, the monocytes are circulating monocytes. In other embodiments, the monocytes are extravasated from the bloodstream to other tissues.

In some embodiments, alterations in the biomarkers of mitochondrial physiology of monocytes can be determined using assays that measure disruption in oxidative phosphorylation. In some embodiments, disruption in oxidative phosphorylation is determined using assays that measure CoQ10 levels, uncoupling ratio, net routine flux control ratio, leak flux control ratio or phosphorylation respiratory control ratio. In some embodiments, alterations in the biomarkers of mitochondrial physiology of monocytes can be determined by measuring alterations in the levels of one or more biomarkers of mitochondrial physiology in a sample of monocytes. In some embodiments, biomarkers of mitochondrial physiology are selected from the group consisting of consisting of lactic acid (lactate) levels, pyruvic acid (pyruvate) levels, lactate/pyruvate ratios, phosphocreatine levels, NADH (NADH+H$^{30}$) or NADPH (NADPH+H$^{30}$) levels; NAD or NADP levels; ATP levels; reduced coenzyme Q (CoQred) levels; oxidized coenzyme Q (CoQox) levels; total coenzyme Q (CoQtot) levels; oxidized cytochrome C levels; reduced cytochrome C levels; oxidized cytochrome C/reduced cytochrome C ratio; acetoacetate levels; beta-hydroxy butyrate levels; acetoacetate/beta-hydroxy butyrate ratio; 8-hydroxy-2'-deoxyguanosine (8-OHdG) levels; levels of reactive oxygen species; oxygen consumption (VO2), carbon dioxide output (VCO2), and respiratory quotient (VCO2/VO2).

In some embodiments, the disease or condition characterized by mitochondrial dysfunction is ischemia, stroke, renal injury, neurodegenerative disease, atherosclerosis, metabolic syndrome, acute myocardial infarction, heart failure, ischemia reperfusion, ureteral obstruction, diabetic nephropathy, diabetes, Leber's Heredity Optic Neuropathy (LHON), Dominant Optic Atrophy (DOA), Barth's syndrome, POLG disease, or Leigh's disease. In some embodiments, the neurodegenerative disease is Alzheimer's disease, Amyotrophic Lateral Sclerosis (ALS), Huntington's disease, Friedreich's ataxia or Multiple Sclerosis.

In some embodiments, the methods described herein use isolated monocytes to detect the amelioration, suppression or prevention of a disease or condition characterized by mitochondrial dysfunction in a subject that has been administered effective amounts of a therapeutic agent such as an aromatic-cationic peptide of the present technology.

In some embodiments, isolated monocytes are useful in detecting a decrease in intracellular ROS (reactive oxygen species) and an increase in cell survival in a subject that has been administered effective amounts of a therapeutic agent such as an aromatic-cationic peptide of the present technology.

In some embodiments, isolated monocytes are useful in detecting an increase in cell viability in a subject that has been administered effective amounts of a therapeutic agent such as an aromatic-cationic peptide of the present technology.

In some embodiments, isolated monocytes are useful in detecting a decrease in the percentage of cells showing increased caspase activity in a subject that has been administered effective amounts of a therapeutic agent such as an aromatic-cationic peptide of the present technology.

In some embodiments, isolated monocytes are useful in detecting a reduction in the rate of ROS accumulation in a subject that has been administered effective amounts of a therapeutic agent such as an aromatic-cationic peptide of the present technology.

In some embodiments, isolated monocytes are useful in detecting suppression of mitochondrial depolarization and ROS accumulation in a subject that has been administered effective amounts of a therapeutic agent such as an aromatic-cationic peptide of the present technology.

In some embodiments, isolated monocytes are useful in detecting inhibition of lipid peroxidation in a subject that has been administered effective amounts of a therapeutic agent such as an aromatic-cationic peptide of the present technology.

In some embodiments, isolated monocytes are useful in detecting a decrease in apoptosis in a subject that has been administered effective amounts of a therapeutic agent such as an aromatic-cationic peptide of the present technology.

In some embodiments, isolated monocytes are useful in detecting a reduction in the disruption in oxidative phosphorylation in a subject that has been administered effective amounts of a therapeutic agent such as an aromatic-cationic peptide of the present technology.

Use of Monocytes to Detect the Modulation of Biomarkers of Mitochondrial Physiology in Response to Treatment The methods of the present technology can be used in subjects or patients to detect the modulation of one or more biomarkers of mitochondrial physiology in a sample of monocytes in response to treatment with an active agent (e.g., an aromatic-cationic peptide). Modulation of biomarkers of mitochondrial physiology can be done to normalize biomarkers of mitochondrial physiology in a subject, or to enhance biomarkers of mitochondrial physiology in a subject.

In one embodiment, the biomarker levels are modulated to a value within about 2 standard deviations of the value in a healthy subject. In another embodiment, the biomarker levels are modulated to a value within about 1 standard deviation of the value in a healthy subject. In another embodiment, the biomarker levels in a subject are changed by at least about 15% above or below the level in the subject prior to administration of the active agent (e.g., an aromatic-cationic peptide). In another embodiment, the biomarker levels are changed by at least about 20% above or below the level in the subject prior to administration of the active agent (e.g., an aromatic-cationic peptide). In another embodiment, the biomarker levels are changed by at least about 30% above or below the level in the subject prior to administration of the active agent (e.g., an aromatic-cationic peptide). In another embodiment, the biomarker levels are changed by at least about 40% above or below the level in the subject prior to administration of the active agent (e.g., an aromatic-cationic peptide). In another embodiment, the biomarker levels are changed by at least about 50% above or below the level in the subject prior to administration of the active agent (e.g., an aromatic-cationic peptide). In another embodiment, the biomarker levels are changed by at least about 75% above or below the level in the subject prior to administration of the active agent (e.g., an aromatic-cationic peptide). In another embodiment, the biomarker levels are changed by at least about 90% above or below the level in the subject prior to administration of the active agent (e.g., an aromatic-cationic peptide). In another embodiment, the biomarker levels are changed by at least about 100% above or below the level in the subject prior to administration of the active agent (e.g., an aromatic-cationic peptide).

Normalization of one or more biomarkers of mitochondrial physiology is defined as either restoring the level of one or more such biomarkers of mitochondrial physiology to normal or near-normal levels in a subject whose levels of one or more biomarkers of mitochondrial physiology show pathological differences from normal levels (i.e., levels in a healthy subject), or to change the levels of one or more biomarkers of mitochondrial physiology to alleviate pathological symptoms in a subject. Depending on the nature of the biomarker of mitochondrial physiology, such levels may show measured values either above or below a normal value. For example, a pathological lactate level is typically higher than the lactate level in a normal (i.e., healthy) person, and a decrease in the level may be desirable. A pathological ATP level is typically lower than the ATP level in a normal (i.e., healthy) person, and an increase in the level of ATP may be desirable. Accordingly, normalization of biomarkers of mitochondrial physiology can involve restoring the level of biomarkers of mitochondrial physiology to within about at least two standard deviations of normal in a subject, or to within about at least one standard deviation of normal in a subject, to within about at least one-half standard deviation of normal, or to within about at least one-quarter standard deviation of normal.

When an increase in the level of one or more biomarkers of mitochondrial physiology is desired to normalize one or more biomarkers of mitochondrial physiology, the level of the one or more biomarkers of mitochondrial physiology can be increased to within about at least two standard deviations of normal in a subject, increased to within about at least one standard deviation of normal in a subject, increased to within about at least one-half standard deviation of normal, or increased to within about at least one-quarter standard deviation of normal, by administration of one or more compounds according to the present technology. Alternatively, the level of one or more of the biomarkers of mitochondrial physiology can be increased by about at least 15% above the subject's level of the respective one or more biomarkers of mitochondrial physiology before administration; by at least 20% above the subject's level of the respective one or more biomarkers of mitochondrial physiology before administration, by at least 30% above the subject's level of the respective one or more biomarkers of mitochondrial physiology before administration, by about at least 40% above the subject's level of the respective one or more biomarkers of mitochondrial physiology before administration, by about at least 50% above the subject's level of the respective one or more biomarkers of mitochondrial physiology before administration, by about at least 75% above the subject's level of the respective one or more biomarkers of mitochondrial physiology before administration, or by about at least 100% above the subject's level of the respective one or more biomarkers of mitochondrial physiology before administration.

When a decrease in the level of one or more biomarkers of mitochondrial physiology is desired to normalize one or more biomarkers of mitochondrial physiology, the level of the one or more biomarkers of mitochondrial physiology can be decreased to a level within about at least two standard deviations of normal in a subject, decreased to within about at least one standard deviation of normal in a subject, decreased to within about at least one-half standard deviation of normal, or decreased to within about at least one-quarter standard deviation of normal, by administration of one or more compounds according to the present technology. Alternatively, the level of the one or more biomarkers of mitochondrial physiology can be decreased by about at least 15% below the subject's level of the respective one or more biomarkers of mitochondrial physiology before administration, by about at least 20% below the subject's level of the respective one or more biomarkers of mitochondrial physiology before administration, by about at least 30% below the subject's level of the respective one or more biomarkers of mitochondrial physiology before administration, by about at least 40% below the subject's level of the respective one or more biomarkers of mitochondrial physiology before administration, by about at least 50% below the subject's level of the respective one or more biomarkers of mitochondrial physiology before administration, by about at least 75% below the subject's level of the respective one or more biomarkers of mitochondrial physiology before administration, or by about at least 90% below the subject's level of the respective one or more biomarkers of mitochondrial physiology before administration.

Enhancement of the level of one or more biomarkers of mitochondrial physiology is defined as changing the extant levels of one or more biomarkers of mitochondrial physiology in a subject to a level which provides beneficial or desired effects for the subject. Sometimes normalization of biomarkers of mitochondrial physiology may not achieve the optimum state for a subject with a disease or condition characterized by mitochondrial dysfunction, and such subjects can also benefit from enhancement of biomarkers of mitochondrial physiology. FIG. 2 illustrates the effect that various dysfunctions can have on biochemistry and biomarkers of mitochondrial physiology.

V Monitoring Disease Progression and Therapeutic Efficacy

The methods of the present technology are useful in assessing the status of treatment or suppression of a disease or condition characterized by mitochondrial dysfunction. For the purposes of monocyte screening, any one or more of the biomarkers of mitochondrial physiology described herein provide conveniently measurable benchmarks by which to gauge the effectiveness of treatment or suppressive therapy. Additionally, other indicators of mitochondrial physiology are known to those skilled in the art and can be monitored to evaluate the efficacy of treatment or suppressive therapy via the methods of monocyte screening described herein.

In some embodiments, the disclosure provides a method for evaluating the efficacy of both prophylactic and therapeutic regimens of a subject having or suspected of having a disease or condition characterized by mitochondrial dysfunction via monocyte screening. For example, in some embodiments, the disclosure provides a method for evaluating the efficacy of both prophylactic and therapeutic regimens of a subject having a disruption in oxidative phosphorylation. In some embodiments, monocytes are assayed via high throughput bioenergetics platforms in order to monitor the treatment of subjects that either have or are predisposed to having a disease or condition characterized by mitochondrial dysfunction. In some embodiments, these high throughput bioenergetics platforms permit the testing of multiple conditions per assay well. In certain embodiments, the high throughput bioenergetics platforms are capable of detecting the synergistic interaction of two or more co-administered compounds.

In some embodiments, a course of treatment is recommended based on the observed alterations in levels and/or biomarkers of mitochondrial physiology of monocytes in a subject having or suspected of having a disease or condition characterized by mitochondrial dysfunction. In some embodiments, the course of treatment is recommended prior to administration of a therapeutic agent, such as an aromatic-cationic peptide of the present technology. In some embodiments, the course of treatment is recommended after administration of a therapeutic agent, such as an aromatic-cationic peptide of the present technology. In some embodiments, the course of treatment is recommended during the administration of a therapeutic agent, such as an aromatic-cationic peptide of the present technology.

The methods described herein are also particularly useful to monitor progression of a disease or condition characterized by mitochondrial dysfunction. This is because the physiological signature of circulating monocytes retains plasticity. Monocytes will exhibit alterations in biomarkers of mitochondrial physiology when exposed to an inflammatory stimulus in the body (e.g., ischemia, stroke, renal injury, atherosclerosis, metabolic syndrome, acute myocardial infarction, heart failure, ischemia reperfusion, ureteral obstruction, diabetic nephropathy, diabetes, Leber's Heredity Optic Neuropathy (LHON), Dominant Optic Atrophy (DOA), Barth's syndrome, POLG disease, Leigh's disease, and neurodegenerative diseases such as Alzheimer's disease, Amyotrophic Lateral Sclerosis (ALS), Friedreich's ataxia, Huntington's disease or Multiple Sclerosis). However, elimination of the stimulus will cause monocytes to revert their physiological profile to baseline values, and vice versa when the stimulus is reintroduced. Thus, according to particular embodiments, the methods provided herein are used for monitoring the progression or recurrence of a disease or condition characterized by mitochondrial dysfunction. This is particularly envisaged for monitoring subjects who are at high risk of recurrence (for example, patients that are genetically predisposed to LHON or have a history of heart failure or stroke).

In certain embodiments, the methods described herein are useful in identifying patient populations that exhibit different degrees of sensitivities to a therapeutic agent (e.g., an aromatic-cationic peptide). Age, gender, height, weight, ethnicity, family history of genetic disorders, immunocompromised status, and medical history are non-limiting examples of factors that can impact responsiveness of a patient to a particular therapeutic agent. Alterations in levels and/or biomarkers of mitochondrial physiology of monocytes can be used to classify patients based on their responsiveness to a specific dose of a therapeutic agent (e.g., an aromatic-cationic peptide). In some embodiments, a patient may be responsive, non-responsive, or hyper-responsive to a therapeutic agent (e.g., an aromatic-cationic peptide) at a specific dose or a range of doses. In some embodiments, monocytes are assayed via high throughput bioenergetics platforms in order to identify responders, non-responders and hyper-responders to a therapeutic agent (e.g., an aromatic-cationic peptide).

Determining patient sensitivity to a therapeutic agent (e.g., an aromatic-cationic peptide) is useful in optimizing therapeutic efficacy and reducing side effects associated with the therapeutic agent. In certain embodiments, the dose of the therapeutic agent (e.g., an aromatic-cationic peptide) may be adjusted to achieve therapeutic efficacy and/or minimize side effects based on alterations in levels and/or biomarkers of mitochondrial physiology of monocytes in treated patients. In other embodiments, a therapeutic agent (e.g., an aromatic-cationic peptide) may be supplemented with an additional therapeutic agent to achieve therapeutic efficacy and/or minimize side effects based on alterations in levels and/or biomarkers of mitochondrial physiology of monocytes in treated patients. In another embodiment, treatment with a therapeutic agent (e.g., an aromatic-cationic peptide) may be temporarily or completely discontinued to achieve therapeutic efficacy and/or minimize side effects based on alterations in levels and/or biomarkers of mitochondrial physiology of monocytes in treated patients.

VI Modes of Administration and Effective Dosages

Any method known to those in the art for contacting a cell, organ or tissue with an active agent such as an aromatic-cationic peptide of the present technology may be employed. Suitable methods include in vitro, ex vivo, or in vivo methods.

In vitro methods typically include cultured samples. For example, a cell can be placed in a reservoir (e.g., tissue culture plate), and incubated with a compound under appropriate conditions suitable for obtaining the desired result. Suitable incubation conditions can be readily determined by those skilled in the art.

Ex vivo methods typically include cells, organs or tissues removed from a mammal, such as a human. The cells, organs or tissues can, for example, be incubated with the compound under appropriate conditions. The contacted cells, organs or tissues are typically returned to the donor, placed in a recipient, or stored for future use. Thus, the compound is generally in a pharmaceutically acceptable carrier.

In vivo methods typically include the administration of an active agent such as an aromatic-cationic peptide of the present technology, such as those described above, to a mammal, suitably a human. When used in vivo for therapy, the active agent such as an aromatic-cationic peptide of the present technology may be administered to the subject in effective amounts (i.e., amounts that have desired therapeutic effect). The dose and dosage regimen will depend upon the degree of the infection in the subject, the characteristics of the particular active agent such as an aromatic-cationic peptide of the present technology used, e.g., its therapeutic index, the subject, and the subject's history.

The effective amount may be determined during preclinical trials and clinical trials by methods familiar to physicians and clinicians. An effective amount of an active agent such as an aromatic-cationic peptide of the present technology useful in the methods may be administered to a mammal in need thereof by any of a number of well-known methods for administering pharmaceutical compounds. The active agent such as an aromatic-cationic peptide may be administered systemically or locally.

The aromatic-cationic peptide of the present technology may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when an aromatic-cationic peptide of the present technology contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glutamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucuronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the salt is an acetate, tartrate or trifluoroacetate salt.

The active agent such as an aromatic-cationic peptide of the present technology described herein can be incorporated into pharmaceutical compositions for administration, singly or in combination, to a subject for the treatment or prevention of a medical disease or condition described herein. Such compositions typically include the active agent (e.g., an aromatic-cationic peptide) and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The active agent such as an aromatic-cationic peptide of the present technology can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, isotonic agents are included, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the active agent such as an aromatic-cationic peptide of the present technology can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of an active agent such as an aromatic-cationic peptide of the present technology as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

An active agent such as an aromatic-cationic peptide of the present technology can be formulated in a carrier system. The carrier can be a colloidal system. The colloidal system can be a liposome, a phospholipid bilayer vehicle. In one embodiment, the therapeutic agent such as an aromatic-cationic peptide is encapsulated in a liposome while maintaining peptide integrity. One skilled in the art would appreciate that there are a variety of methods to prepare liposomes. See Lichtenberg, et al., *Methods Biochem. Anal.,* 33:337-462 (1988); Anscicm, et al., *Liposome Technology,* CRC Press (1993)). Liposomal formulations can delay clearance and increase cellular uptake (See Reddy, *Ann. Pharmacother.,* 34(7-8):915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the active agent such as an aromatic-cationic peptide of the present technology can be embedded in the polymer matrix, while maintaining protein integrity. The polymer may be natural, such as polypeptides, proteins or polysaccharides, or synthetic, such as poly a-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.,* 34(7-8):915-923 (2000)). A polymer formulation for human growth hormone (hGH) has been used in clinical trials. See Kozarich and Rich, *Chemical Biology,* 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zalc, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the active agents such as an aromatic-cationic peptide of the present technology are prepared with carriers that will protect the active agent (e.g., aromatic-cationic peptide of the present technology) against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The active agent such as an aromatic-cationic peptide of the present technology can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods,* 4(3): 201-9 (1994); and Gregoriadis, "Engineering Liposomes for Drug Delivery: Progress and Problems," *Trends Biotechnol.,* 13(12):527-37 (1995). Mizguchi, et al., *Cancer Lett.,* 100: 63-69 (1996), describes the use of fusogenic liposomes to deliver a protein to cells both in vivo and in vitro.

Dosage, toxicity and therapeutic efficacy of the active agent such as an aromatic-cationic peptide of the present technology can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In some embodiments, the active agent such as an aromatic-cationic peptide of the present technology exhibit high therapeutic indices. While an active agent such as an aromatic-cationic peptide of the present technology that exhibits toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies within a range of circulating concentrations that include the ED50 with little or no toxicity. The dosage may vary within this range depending upon the dosage form employed and the route of administration utilized. For any active agent (e.g., an aromatic-cationic peptide of the present technology) used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of the active agent such as an aromatic-cationic peptide of the present technology, sufficient for achieving a therapeutic or prophylactic effect, ranges from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of an active agent such as an aromatic-cationic peptide, ranges from 0.001-10,000 micrograms per kg body weight. In one embodiment, active agent (e.g., aromatic-cationic peptide) concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, and until the subject shows partial or complete amelioration of symptoms of disease. Thereafter, the patient can be administered a prophylactic regime.

In some embodiments, a therapeutically effective amount of an active agent such as an aromatic-cationic peptide of the present technology may be defined as a concentration of agent (e.g., peptide) at the target tissue of $10^{-12}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue. In some embodiments, the doses are administered by single daily or weekly administration, but may also include continuous administration (e.g., parenteral infusion or transdermal application). In some embodiments, the dosage of the active agent (e.g., aromatic-cationic peptide of the present technology) is provided at a "low," "mid," or "high" dose level. In one embodiment, the low dose is provided from about 0.0001 to about 0.5 mg/kg/h, suitably from about 0.001 to about 0.1 mg/kg/h. In one embodiment, the mid-dose is provided from about 0.01 to about 1.0 mg/kg/h, suitably from about 0.01 to about 0.5 mg/kg/h. In one embodiment, the high dose is provided from about 0.5 to about 10 mg/kg/h, suitably from about 0.5 to about 2 mg/kg/h.

The skilled artisan will appreciate that certain factors may influence the dosage and timing required to effectively treat a subject, including but not limited to, the severity of the medical disease or condition, previous treatments, the general health and/or age of the subject, and other diseases present. Moreover, treatment of a subject with a therapeutically effective amount of the therapeutic compositions described herein can include a single treatment or a series of treatments.

The mammal treated in accordance present methods can be any mammal, including, for example, farm animals, such as sheep, pigs, cows, and horses; pet animals, such as dogs and cats; laboratory animals, such as rats, mice and rabbits. In some embodiments, the mammal is a human.

VII Evaluating the Efficacy of Combination Therapy with an Aromatic-Cationic Peptide of the Present Technology and Other Therapeutic Agents In some embodiments, the methods of the present technology are capable of detecting the synergistic interaction of two or more co-administered compounds (e.g., an aromatic-cationic peptide and an additional therapeutic agent).

In one embodiment, an additional therapeutic agent is administered to a subject in combination with an aromatic-cationic peptide of the present technology, such that a synergistic therapeutic effect is produced. A "synergistic therapeutic effect" refers to a greater-than-additive therapeutic effect which is produced by a combination of two therapeutic agents, and which exceeds that which would otherwise result from individual administration of either therapeutic agent alone. Therefore, lower doses of one or both of the therapeutic agents may be used in treating a medical disease or condition, e.g., disruptions in mitochondrial oxidative phosphorylation, resulting in increased therapeutic efficacy and decreased side-effects.

The multiple therapeutic agents (including, but not limited to, e.g., aromatic-cationic peptide of the present technology) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

EXAMPLES

The present technology is further illustrated by the following examples, which should not be construed as limiting in any way. For each of the examples below, any aromatic-cationic peptide described herein could be used. By way of example, but not by limitation, the aromatic-cationic peptide used in the examples below could be 2'6'-Dmt-D-Arg-Phe-Lys-NH$_2$, Phe-D-Arg-Phe-Lys-NH$_2$, D-Arg-2'6'-Dmt-Lys-Phe-NH$_2$ or any one or more of the peptides shown in Section II.

Example 1

Diagnosing Transient Ischemic Stroke in a Subject Using Monocyte Screening

This Example will demonstrate the use of monocyte screening in diagnosing transient ischemic stroke events in a subject.

Fifty patients with a reported history of transient ischemic stroke and ten age-matched non-stroke controls will be selected for a clinical study. Exclusion criteria will include concurrent infection, tumor bearing state, history of chronic inflammatory disease, use of drugs such as antibiotics, immunosuppressants, and steroids within the preceding 3 months. Blood samples are obtained from all patients after obtaining informed consent.

The stroke and control patients will be repeatedly tested for the proportions of monocyte subsets in blood samples over a thirty day period. Ethylenediaminetetraacetic acid (EDTA)-anticoagulated venous blood samples are collected from the subjects prior to each analysis. After separating mononuclear cells, monocytes are stained using fluorescein isothiocyanate (FITC)-labelled anti-CD16 and phycoerythrin/cyanin 7 (PE-Cy7)-conjugated anti-CD14 monoclonal antibodies (BD Biosciences, San Jose, USA), and then analyzed with a BD FACSCanto flow cytometer (BD Biosciences, San Jose, USA). Determination of CD14 and CD16 positivity will be made using the appropriate isotype control antibody in keeping with the current consensus. Monocyte subsets are defined as $CD14^{high}CD16^-$ classical, $CD14^{high}CD16^+$ intermediate, and $CD14^{low}CD16^{high}$ non-classical monocytes. Alterations in the biomarkers of mitochondrial physiology of these isolated monocytes will be subsequently assessed using an $XF^e$ Analyzer (Seahorse Biosciences). Patients that show elevated counts of classical and intermediate monocytes will be subjected to ultrasound scans and Doppler-flow studies.

It is anticipated that the rate of transient ischemic attacks will be significantly higher in stroke patients with elevated counts of classical and intermediate monocytes compared to stroke patients with a reduced count of classical and intermediate monocytes. It is also anticipated that the overall monocyte count of the stroke group will be higher compared to that observed in the control group. Additionally, the stroke patients are expected to show an increase in disruption of oxidative phosphorylation (as well as other abnormalities in the biomarkers of mitochondrial physiology) compared to the age-matched controls.

These results will show that methods that evaluate the overall count, distribution and biomarkers of mitochondrial physiology of monocytes are useful as methods for diagnosing transient ischemic stroke events in a subject. The results will show that the methods described herein are generally useful in diagnosing a subject as having a disease or condition characterized by mitochondrial dysfunction.

Example 2

Determining Therapeutic Efficacy of Aromatic-Cationic Peptides in a Mouse Model of Huntington's Disease Using Monocyte Screening This Example will show that monocyte screening methods of the present technology can be used to determine the therapeutic efficacy of aromatic-cationic peptides in reducing neurological defects associated with Huntington's Disease (HD).

R6/2 mice, expressing exon 1 of the human HD gene carrying more than 120 CAG repeats, exhibit progressive neurological phenotypes that mimic the features of HD in humans. The mice develop progressive neurological phenotypes gradually with mild phenotype (e.g., resting tremor) as early as 5 weeks of age and severe symptoms (including reduced mobility and seizures) at 9-11 weeks, with many of the mice dying by 14 weeks.

R6/2 HD transgenic mice are treated with an empty vehicle; or an aromatic-cationic peptide, using Alzet osmotic mini-pumps (delivering 3 mg/kg/day) from age 5 weeks to 13 weeks. Monocytes are isolated from blood samples that are drawn every third day during the 5-14 week stage. The biomarkers of mitochondrial physiology of the isolated monocytes will be assessed by simultaneously measuring the basal oxygen consumption, glycolysis rates, ATP production, and respiratory capacity via the XF technology platform (Seahorse Biosciences). The R6/2 HD transgenic animals will also be subjected to a number of behavioral assessments to study motor and cognitive function. Rotor-rod and mobility in an activity chamber are used for assessment of motor function, and the Y-maze is used for assessment of working memory.

Results—It is anticipated that vehicle-treated R6/2 mice will show disruption in oxidative phosphorylation along with major motor deficits. It is further anticipated that treatment with the aromatic-cationic peptide will reduce the disruption in oxidative phosphorylation in isolated monocytes, while simultaneously improving motor activity and cognitive function in the R6/2 mice (as demonstrated by the animals' performance in the Y-maze test).

These results will show that methods that evaluate the biomarkers of mitochondrial physiology of monocytes are useful as methods for determining the therapeutic efficacy of aromatic-cationic peptides in reducing neurological defects of HD. The results will show that the methods described herein are generally useful in evaluating the efficacy of therapeutic agents on a disease or condition characterized by mitochondrial dysfunction.

Example 3

Determining Disease Progression and Therapeutic Efficacy of Aromatic-Cationic Peptides in Huntington's Disease Patients Using Monocyte Screening This Example will show that monocyte screening methods of the present technology can be used to monitor disease progression and determine the therapeutic efficacy of aromatic-cationic peptides in reducing neurological defects associated with Huntington's Disease (HD) in human patients.

HD patients exhibit progressive neurological phenotypes over time ranging from mild phenotypes (e.g., resting tremor) to extreme neurological symptoms (including reduced mobility and seizures).

Patients diagnosed with mid-stage HD are treated with an empty vehicle; or an aromatic-cationic peptide at a concentration of 10 mg/kg/day, for a period of 2 months. Monocytes are isolated from blood samples that are drawn every third day during the 2 month treatment period. The biomarkers of mitochondrial physiology of the isolated monocytes will be assessed by simultaneously measuring the basal oxygen consumption, glycolysis rates, ATP production, and respiratory capacity via the XF technology platform (Seahorse Biosciences).

Results—It is anticipated that vehicle-treated HD patients will show an increase in the disruption in oxidative phosphorylation in monocytes while simultaneously experiencing an exacerbation of neurological deficits over the 2 month period. It is further anticipated that patients treated with the aromatic-cationic peptide will show a reduction in the disruption in oxidative phosphorylation in isolated monocytes, and a concomitant improvement in motor activity.

These results will show that methods that evaluate the biomarkers of mitochondrial physiology of monocytes are useful as methods for determining the therapeutic efficacy of aromatic-cationic peptides in reducing neurological defects of HD. These methods are also useful in monitoring the progression of HD. The results will show that the methods described herein are generally useful in evaluating the efficacy of therapeutic agents on a disease or condition characterized by mitochondrial dysfunction and monitoring disease progression.

Example 4

Determining Therapeutic Efficacy of Aromatic-Cationic Peptides in Subjects with Chronic Heart Failure Using Monocyte Screening This example will show that monocyte screening methods of the present technology can be used to determine the therapeutic efficacy of aromatic-cationic peptides in treating chronic heart failure in a dog model.

Peripheral blood samples were obtained from 6 normal dogs and 6 dogs with coronary microembolizations-induced heart failure (LV ejection fraction ~30%). Monocytes were isolated from the peripheral blood samples via sequential Ficoll and Percoll density gradients. Monocyte viability, assayed using Trypan blue exclusion, was ~70%. An XFc/XF96 analyzer (Scahorsc Bioscience) was used to measure oxygen consumption rates (OCR) in monocytes in the presence and absence of 1 µM oligomycin, 0.5 µM FCCP, or 1 µM each rotenone and antimycin. Mitochondrial proton leak, maximal respiration (MAXresp) and spare respiratory capacity (SRC) were measured in the presence and absence of 0.1, 1.0 and 10 µM concentrations of D-Arg-2'6'Dmt-Lys-Phe-NH$_2$. Results were expressed in pmols OCR/min/µg protein.

As shown in Table 8, proton leak, MAXresp and SRC were abnormal in the circulating monocytes of heart failure dogs compared to normal dogs. Incubation with D-Arg-2'6'Dmt-Lys-Phe-NH$_2$ had no effect on any of the measures of monocyte mitochondrial function of normal dogs. In contrast, the monocyte mitochondrial function of heart failure dogs was nearly normalized/restored after treatment with D-Arg-2'6'Dmt-Lys-Phe-NH$_2$, as evidenced by the dose-dependent increase in MAXresp and SRC, and dose-dependent decrease in proton leak (Table 8). These results are consistent with the time course experiments shown in FIG. 1.

results show that the methods described herein are generally useful in evaluating the efficacy of therapeutic agents such as aromatic-cationic peptides on a disease or condition characterized by mitochondrial dysfunction.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having

TABLE 8

| | Monocytes from Normal Dogs | | | | Monocytes from Heart Failure Dogs | | | |
|---|---|---|---|---|---|---|---|---|
| Peptide concentration | 0.0 µM | 0.1 µM | 1.0 µM | 10 µM | 0.0 µM | 0.1 µM | 1.0 µM | 10 µM |
| Proton Leak (pmols OCR/min/µg protein) | 0.49 ± 0.04 | 0.54 ± 0.22 | 0.47 ± 0.06 | 0.48 ± 0.03 | 2.06 ± 0.23 | 1.55 ± 0.20* | 0.94 ± 0.12* | 0.77 ± 0.04* |
| MAXresp (pmols OCR/min/µg protein) | 11.4± 0.62 | 11.1 ± 0.74 | 12.1 ± 0.84 | 12.1 ± 0.67 | 5.5 ± 0.14 | 6.3 ± 0.23 | 8.3 ± 0.20* | 9.4 ± 0.78* |
| SRC (pmols OCR/min/µg protein) | 6.75 ± 0.55 | 6.35 ± 0.64 | 7.04 ± 0.92 | 7.04 ± 0.58 | 1.42 ± 0.14 | 1.95 ± 0.20 | 3.64 ± 0.36* | 4.51 ± 0.70* |

*= p < 0.05 vs. 0.0 µM D-Arg-2'6'Dmt-Lys-Phe-NH$_2$

These results support the use of circulating monocytes as means of assessing the therapeutic efficacy of aromatic-cationic peptides of the present technology in treating chronic heart failure. These methods are also useful in monitoring the progression of chronic heart failure. The 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for evaluating the therapeutic efficacy of an aromatic-cationic peptide on a disease or condition characterized by mitochondrial dysfunction in a subject, comprising:
   (a) assaying the level of a population of activated monocytes present in a biological sample obtained from the subject; and
   (b) comparing the level of the population of activated monocytes observed in step (a) with the level of a corresponding population of activated monocytes observed in a biological sample obtained from the subject following administration of a dose of an aromatic-cationic peptide,
   wherein the aromatic-cationic peptide is identified as having a therapeutic effect on the population of activated monocytes in the biological sample following the administration of the aromatic-cationic peptide is reduced compared to the level of the population of activated monocytes observed in step (a), and wherein thedisease is Barth Syndrome.

2. The method of claim 1, wherein the subject is human.

3. The method of claim 1, wherein the aromatic-cationic peptide is Phe-D-Arg-Phe-Lys-$NH_2$ or D-Arg-2'6'Dmt-Lys-Phe-$NH_2$ or a pharmaceutically acceptable salt thereof.

4. The method of claim 1, wherein the level of classical monocytes ($CD14^{high}$ $CD16^-$) in the biological sample following the administration of the aromatic-cationic peptide is reduced compared to the level of classical monocytes observed in step (a).

5. The method of claim 1, wherein the level of intermediate monocytes ($CD14^{high}$ $CD16^+$) in the biological sample following the administration of the aromatic-cationic peptide is reduced compared to the level of intermediate monocytes observed in step (a).

6. The method of claim 1, wherein the level of non-classical monocytes ($CD14^{low}$ $CD16^{high}$) in the biological sample following the administration of the aromatic-cationic peptide is increased compared to the level of non-classical monocytes observed in step (a).

7. A method for evaluating the therapeutic efficacy of an aromatic-cationic peptide on a disease or condition characterized by mitochondrial dysfunction in a subject, comprising:
   (a) assaying the ratio of different monocyte types present in a biological sample obtained from the subject; and
   (b) comparing the ratio of different monocyte types observed in step (a) with the ratio of corresponding monocyte types observed in a biological sample obtained from the subject following administration of a dose of an aromatic-cationic peptide,
   wherein the aromatic-cationic peptide is identified as having a therapeutic effect on the disease or condition characterized by mitochondrial dysfunction if the ratio of different monocyte types in the biological sample following the administration of the aromatic-cationic peptide is altered compared to the ratio of different monocyte types observed in step (a), and wherein the disease is Barth Syndrome.

8. The method of claim 7, wherein the subject is human.

9. The method of claim 7, wherein the aromatic-cationic peptide is Phe-D-Arg-Phe-Lys-$NH_2$ or D-Arg-2'6'Dmt-Lys-Phe-$NH_2$ or a pharmaceutically acceptable salt thereof.

10. The method of claim 7, wherein the ratio of classical monocytes to non-classical monocytes in the biological sample following the administration of the aromatic-cationic peptide is reduced compared to the ratio of classical monocytes to non-classical monocytes observed in step (a).

11. The method of claim 7, wherein the ratio of intermediate monocytes to non-classical monocytes in the biological sample following the administration of the aromatic-cationic peptide is reduced compared to the ratio of intermediate monocytes to non-classical monocytes observed in step (a).

12. The method of claim 7, wherein the ratio of classical monocytes to intermediate monocytes in the biological sample following the administration of the aromatic-cationic peptide is reduced compared to the ratio of classical monocytes to intermediate monocytes observed in step (a).

13. A method for evaluating the therapeutic efficacy of an aromatic-cationic peptide on a disease or condition characterized by mitochondrial dysfunction in a subject, comprising:
   (a) assaying at least one biomarker of mitochondrial physiology of a population of monocytes present in a biological sample obtained from the subject; and
   (b) comparing the biomarker of mitochondrial physiology of the population of monocytes observed in step (a) with the biomarker of mitochondrial physiology of a corresponding population of monocytes observed in a biological sample obtained from the subject following administration of a dose of an aromatic-cationic peptide,
   wherein the aromatic-cationic peptide is identified as having a therapeutic effect on the disease or condition characterized by mitochondrial dysfunction if the biomarker of mitochondrial physiology of the population of monocytes in the biological sample following the administration of the aromatic-cationic peptide is similar to the biomarker of mitochondrial physiology of a corresponding population of monocytes in a reference sample obtained from a healthy subject, and wherein the disease is Barth Syndrome.

14. The method of claim 13, wherein the subject is human.

15. The method of claim 13, wherein the aromatic-cationic peptide is Phe-D-Arg-Phe-Lys-$NH_2$ or D-Arg-2'6'Dmt-Lys-Phe-$NH_2$ or a pharmaceutically acceptable salt thereof.

16. The method of claim 13, wherein determining the alterations in biomarkers of mitochondrial physiology is by assaying the disruption in oxidative phosphorylation.

17. The method of claim 16, wherein determining the disruption in oxidative phosphorylation is by assaying the CoQ10 levels, uncoupling ratio, net routine flux control ratio, leak flux control ratio or phosphorylation respiratory control ratio.

18. The method of claim 13, wherein the alterations in biomarkers of mitochondrial physiology of monocytes is determined by measuring alterations in the level of one or more biomarkers of mitochondrial physiology in a sample of monocytes.

19. The method of claim 18, wherein the biomarkers of mitochondrial physiology are selected from the group consisting of lactic acid (lactate) levels; pyruvic acid (pyruvate) levels; lactate/pyruvate ratios; phosphocreatine levels; NADH (NADH+$H^{30}$) levels; NADPH (NADPH+$H^{30}$) levels; NAD levels; NADP levels; ATP levels; reduced coenzyme Q (CoQred) levels; oxidized coenzyme Q (CoQox)

levels; total coenzyme Q (CoQtot) levels; oxidized cytochrome C levels; reduced cytochrome C levels; oxidized cytochrome C/reduced cytochrome C ratio; acetoacetate levels; beta-hydroxy butyrate levels; acetoacetate/beta-hydroxy butyrate ratio; 8-hydroxy-2'-deoxyguanosine (8-OHdG) levels; levels of reactive oxygen species; oxygen consumption (VO2); carbon dioxide output (VCO2); and respiratory quotient (VCO2/VO2).

20. The method of claim 13, wherein determining alternations in the biomarkers of mitochondrial physiology is by high throughput bioenergetics platforms.

* * * * *